(12) United States Patent
Campbell et al.

(10) Patent No.: US 10,370,420 B2
(45) Date of Patent: Aug. 6, 2019

(54) GENETICALLY ENCODED PHOTOCLEAVABLE PROTEINS

(71) Applicant: THE GOVERNORS OF THE UNIVERSITY OF ALBERTA, Edmonton (CA)

(72) Inventors: Robert Campbell, Edmonton (CA); Wei Zhang, Edmonton (CA); Hiofan Hoi, Edmonton (CA)

(*) Notice: Subject to any disclaimer, the term of this patent is extended or adjusted under 35 U.S.C. 154(b) by 74 days.

(21) Appl. No.: 15/116,168

(22) PCT Filed: Feb. 10, 2015

(86) PCT No.: PCT/CA2015/050095
§ 371 (c)(1),
(2) Date: Aug. 2, 2016

(87) PCT Pub. No.: WO2015/120548
PCT Pub. Date: Aug. 20, 2015

(65) Prior Publication Data
US 2017/0190749 A1    Jul. 6, 2017

Related U.S. Application Data

(60) Provisional application No. 61/938,483, filed on Feb. 11, 2014.

(51) Int. Cl.
| | |
|---|---|
| *C12N 15/00* | (2006.01) |
| *C12N 1/20* | (2006.01) |
| *C12P 21/06* | (2006.01) |
| *C12P 21/04* | (2006.01) |
| *C07H 21/02* | (2006.01) |
| *C07K 1/00* | (2006.01) |
| *C07K 14/435* | (2006.01) |
| *C07K 1/107* | (2006.01) |

(Continued)

(52) U.S. Cl.
CPC .... *C07K 14/43595* (2013.01); *A01K 67/0275* (2013.01); *C07K 1/107* (2013.01); *C07K 1/22* (2013.01); *C12N 9/00* (2013.01); *C12N 15/635* (2013.01); *G01N 33/6803* (2013.01)

(58) Field of Classification Search
None
See application file for complete search history.

(56) References Cited

U.S. PATENT DOCUMENTS

| | | | |
|---|---|---|---|
| 6,589,736 B1 | 7/2003 | Rothschild et al. | |
| 7,456,022 B2 | 11/2008 | Haramura | |

(Continued)

FOREIGN PATENT DOCUMENTS

EP    1548107    6/2005

OTHER PUBLICATIONS

Hoi. A monomeric photoconvertible fluorescent protein for imaging of dynamic protein localization J Mol Biol. Sep. 3, 2010;401(5):776-91. doi: 10.1016/j.jmb.2010.06.056. Epub Jul. 13, 2010.*

(Continued)

*Primary Examiner* — Yong D Pak
(74) *Attorney, Agent, or Firm* — Bennett Jones LLP

(57) ABSTRACT

Genetically encoded, photocleavable proteins are derived from a fluorescent protein. Upon illumination, the proteins photocleave and spontaneously dissociate into two or more fragments or release one end of an internal loop.

8 Claims, 20 Drawing Sheets

Specification includes a Sequence Listing.

(51) Int. Cl.
  *C07K 1/22* (2006.01)
  *G01N 33/68* (2006.01)
  *A01K 67/027* (2006.01)
  *C12N 9/00* (2006.01)
  *C12N 15/63* (2006.01)

(56) References Cited

U.S. PATENT DOCUMENTS

| | | |
|---|---|---|
| 7,485,427 B1 | 2/2009 | Rothschild et al. |
| 7,923,562 B2 | 4/2011 | Chen et al. |
| 2011/0214192 A1* | 9/2011 | Wang .............. C07K 14/43595 800/13 |

OTHER PUBLICATIONS

Studer. Residue mutations and their impact on protein structure and function: detecting beneficial and pathogenic changes. Residue mutations and their impact on protein structure and function: detecting beneficial and pathogenic changes. Biochem. J. (2013) 449, 581-594.*

McEvoy. mMaple: a photoconvertible fluorescent protein for use in multiple imaging modalities. PLoS One. 2012;7(12):e51314. doi: 10.1371/journal.pone.0051314. Epub Dec 11, 2012.*

Uliel. A simple algorithm for detecting circular permutations in proteins. Bioinformatics. Nov. 1999;15(11):930-6.*

R. Feil et al.; Regulation of Cre Recombinase Activity by Mutated Estrogen Receptor Ligand-Binding Domains; Biochemical and Biophysical Research Communications 237; 752-757; 1997.

J-L Louvion et al.; Fusion of GAL4-VP16 to a steroid-binding domain provides a tool for gratuitous induction of galactose-responsive genes in yeast; Gene, 131; 129-134; 1993.

D. Metzger et al.; Conditional site-specific recombination in mammalian cells using a ligand-dependent chimeric Cre recombinase; Proc. Natl. Acad. Sci. USA; vol. 92, pp. 6991-6995, Jul. 1995.

M. Eilers et al.; Chimaeras of Myc oncoprotein and steroid receptors cause hormone-dependent transformation of cells; Nature; vol. 340; 66-68; Jul. 6, 1989.

S. Braselmann et al.; A selective transcriptional induction system for mammalian cells based on Gal4-estrogen receptor fusion proteins; Proc. Natl. Acad. Sci. USA; vol. 90; 1657-1661, Mar. 1993.

D. Picard et al.; A Movable and Regulable Inactivation Function within the Steroid Binding Domain of the Glucocorticoid Receptor; Cell; vol. 54; 1073-1080; Sep. 23, 1988.

* cited by examiner

Figure 4

*CpPhoCle*
ATGGTGAGCAAGGGCGAGGAGACCATTACGAGCGTGATCAAGCCTGACATGAAGAACAA
GCTGCGCATGGAGGGCAACGTGAACGGCCACGCCTTCGTGATCGAGGGCGAGGGCAGCG
GCAAGCCCTTCGAGGGCATCCAGACGATTGATTTGGAGGTGAAGGAGGGCGCCCCGCTGC
CCTTCGCCTACGACATCCTGACCACCGCCTTCCACTACGGCAACCGCGTGTTCACCAAGTA
CCCACGTAGATCTCCGTCACTTAGAAGTGAGTATGAGTACCCTGTTTTTTCTCATGTTCAG
GCAGGGATGTTCTCACCTAAACTTAGAACCTTTACCAAAGGTGATGCGGAGAGATGGGTA
AGCGGTACCAGTATCCCTGACTACTTCAAGCAGAGCTTCCCCGAGGGCTACAGCTGGGAG
CGCAGCATGACCTACGAGGACGGCGGCATCTGCATCGCCACCAACGACATCACAATGGAG
GAGGACAGCTTCATCAACAAGATCCACTTCAAGGGCACGAACTTCCCCCCCAACGGCCCC
GTGATGCAGAAGAGGACCGTGGGCTGGGAGGTCAGCACCGAGAAGATGTACGTGCGCGA
CGGCGTGCTGAAGGGCGACGTGAAGATGAAGCTGCTGCTGAAGGGCGGCAGCCACTATC
GCTGCGACTTCCGCACCACCTACAAGGTCAAGCAGAAGGCCGTAAAGCTGCCCGACTACC
ACTTCGTGGACCACCGCATCGAGATCCTGAGCCACGACAAGGACTACAACAAGGTGAAGC
TGTACGAGCACGCCGTGGCCCGCAACTCCACCGACAGCATGGACGAGCTGTACAAGTAA
LINKER

FIG. 14A

CpPhoCle
```
atggtgagcaagggcgaggagaccattacgagcgtgatcaagcctgacatgaagaacaag
 M  V  S  K  G  E  E  T  I  T  S  V  I  K  P  D  M  K  N  K
ctgcgcatggagggcaacgtgaacggccacgccttcgtgatcgagggcgagggcagcggc
 L  R  M  E  G  N  V  N  G  H  A  F  V  I  E  G  E  G  S  G
aagcccttcgagggcatccagacgattgatttggaggtgaaggagggcgccccgctgccc
 K  P  F  E  G  I  Q  T  I  D  L  E  V  K  E  G  A  P  L  P
ttcgcctacgacatcctgaccaccgccttccactacggcaaccgcgtgttcaccaagtac
 F  A  Y  D  I  L  T  T  A  F  H  Y  G  N  R  V  F  T  K  Y
ccacgtagatctccgtcacttagaagtgagtatgagtaccctgttttttctcatgttcag
 P  R  R  S  P  S  L  R  S  E  Y  E  Y  P  V  F  S  H  V  Q
gcagggatgttctcacctaaacttagaacctttaccaaaggtgatgcggagagatgggta
 A  G  M  F  S  P  K  L  R  T  F  T  K  G  D  A  E  R  W  V
agcggtaccagtatccctgactacttcaagcagagcttccccgagggctacagctgggag
 S  G  T  S  I  P  D  Y  F  K  Q  S  F  P  E  G  Y  S  W  E
cgcagcatgacctacgaggacggcggcatctgcatcgccaccaacgacatcacaatggag
 R  S  M  T  Y  E  D  G  G  I  C  I  A  T  N  D  I  T  M  E
gaggacagcttcatcaacaagatccacttcaagggcacgaacttcccccccaacggcccc
 E  D  S  F  I  N  K  I  H  F  K  G  T  N  F  P  P  N  G  P
gtgatgcagaagaggaccgtgggctgggaggtcagcaccgagaagatgtacgtgcgcgac
 V  M  Q  K  R  T  V  G  W  E  V  S  T  E  K  M  Y  V  R  D
ggcgtgctgaagggcgacgtgaagatgaagctgctgctgaagggcggcagccactatcgc
 G  V  L  K  G  D  V  K  M  K  L  L  L  K  G  G  S  H  Y  R
tgcgacttccgcaccacctacaaggtcaagcagaaggccgtaaagctgcccgactaccac
 C  D  F  R  T  T  Y  K  V  K  Q  K  A  V  K  L  P  D  Y  H
ttcgtggaccaccgcatcgagatcctgagccacgacaaggactacaacaaggtgaagctg
 F  V  D  H  R  I  E  I  L  S  H  D  K  D  Y  N  K  V  K  L
tacgagcacgccgtggcccgcaactccaccgacagcatggacgagctgtacaagtaa
 Y  E  H  A  V  A  R  N  S  T  D  S  M  D  E  L  Y  K  -
```

FIG. 14B

```
Phocle0.1  atggtgatccctgactacttcaagcagagcttccccgagggctacagctgggagcgcagc
Phocle0.2  atggtgatccctgactacttcaagcagagcttccccgagggctacagctgggagcgcagc
phocle0.3  atggtgatccctgactacttcaagcagagcttccccgagggctacagctgggagcgcagc
phocle0.4  atggtgatccctgactacttcaagcagagcttccccgagggctacagctgggagcgcagc
Phocle0.5  atggtgatccctgactacttcaagcagagcttccccgagggctacagctgggagcgcagc
phocle0.6  atggtgatccctgactacttcaagcagagcttccccgagggctacagctgggagcgcagc
Phocle0.7  atggtgatccctgactacttcaagcagagcttccccgagggctacagctgggagcgcagc
           ************************************************************
Phocle0.1  atgacctacgaggacggcggcatctgcatcgccaccaacgacatcacaatggaggaggac
Phocle0.2  atgacctacgaggacggcggcatctgcatcgccaccaacgacatcacaatggaggaggac
phocle0.3  atgacctacgaggacggcggcatctgcatcgccaccaacgacatcacaatggaggaggac
phocle0.4  atgacctacgaggacggcggcatctgcatcgccaccaacgacatcacaatggaggaggac
Phocle0.5  atgacctacgaggacggcggcatctgcatcgccaccaacgacatcacaatggaggggggac
phocle0.6  atgacctacgaggacggcggcatctgcatcgccaccaacgacatcacaatggaggggggac
Phocle0.7  atgacctacgaggacggcggcatctgcatcgccaccaacgacatcacaatggaggggggac
           ********************************************************.****
Phocle0.1  agcttcatcaacaagatccacttcaagggcacgaacttccccccccaacggcccccgtgatg
Phocle0.2  agcttcatcaacaagatccacttcaagggcacgaacttccccccccaacggcccccgtgatg
phocle0.3  agcttcatcaacaagatccacttcaagggcacgaacttccccccccaacggcccccgtgatg
phocle0.4  agcttcatcaacaagatccacttcaagggcacgaacttccccccccaacggcccccgtgatg
Phocle0.5  agcttcatcaacaagatccacttcaagggcacgaacttccccccccaacggcccccgtgatg
phocle0.6  agcttcatcaacaagatccacttcaagggcacgaacttccccccccaacggcccccgtgatg
Phocle0.7  agcttcatcaacaagatccacttcaagggcacgaacttccccccccaacggcccccgtgatg
           ************************************************************
Phocle0.1  cagaagaggaccgtgggctgggaggtcagcaccgagaagatgtacgtgcgcgacggcgtg
Phocle0.2  cagaagaggaccgtgggctgggaggtcagcaccgagaagatgtacgtgcgcgacggcgtg
phocle0.3  cagaagaggaccgtgggctgggaggtcagcaccgagaagatgtacgtgcgcgacggcgtg
phocle0.4  cagaagaggaccgtgggctgggaggtcagcaccgagaagatgtacgtgcgcgacggcgtg
Phocle0.5  cagaagaggaccgtgggctgggaggccagcaccgagaagatgtacgtgcgcgacggcgtg
phocle0.6  cagaagaggaccgtgggctgggaggccagcaccgagaagatgtacgagcgcgacggcgtg
Phocle0.7  cagaagaggaccgtgggctgggaggccagcaccgagaagatgtacgagcgcgacggcgtg
           **************************.******************** ***********
Phocle0.1  ctgaagggcgacgtgaagatgaagctgctgctgaagggcggcagccactatcgctgcgac
Phocle0.2  ctgaagggcgacgtgaagatgaagctgctgctgaagggcggcagccactatcgctgcgac
phocle0.3  ctgaagggcgacgtgaagatgaagctgctgctgaagggcggcagccactatcgctgcgac
phocle0.4  ctgaagggcgacgtgaagatgaagctgctgctgaagggcggcggccactatcgctgcgac
Phocle0.5  ctgaagggcgacgtgaagatgaagctgctgctgaagggcggcggccactatcgctgcgac
phocle0.6  ctgaagggcgacgtgaagatgaagctgctgctgaagggcggcggccactatcgctgcgac
Phocle0.7  ctgaagggcgacgtgaagatgaagctgctgctgaagggcggcggccactatcgctgcgac
           ******************************************.****************
Phocle0.1  ttccgcaccacctacaaggtcaagcagaaggccgtaaagctgcccgactaccacttcgtg
Phocle0.2  ttccgcaccacctacaaggtcaagcagaaggccgtaaagctgcccgactaccacttcgtg
phocle0.3  taccgcaccacctacaaggtcaagcagaaggccgtaaagctgcccgactaccacttcgtg
phocle0.4  taccgcaccacctacaaggtcaagcagaaggccgtaaagctgcccgactaccacttcgtg
Phocle0.5  taccgcaccacctacaaggtcaagcagaaggccgtaaagctgcccgactcccacttcgtg
phocle0.6  taccgcaccacctacaaggtcaagcagaaggccgtaaagctgcccgactaccacttcgtg
Phocle0.7  taccgcaccacctacaaggtcaagcagaagcccgtaaagctgcccgactaccacttcgtg
           * ***************************  ****************** *********
Phocle0.1  gaccaccgcatcgagatcctgagccacgacaaggactacaacaaggtgaagctgtacgag
Phocle0.2  gaccaccgcatcgagatcctgagccacgacaaggactacaacaaggtgaagctgtacgag
phocle0.3  gaccaccgcatcgagatcctgagccacgacaaggactacaacaaggtgaagctgtacgag
phocle0.4  gaccaccgcatcgagatcctgagccacgacaaggactacaacaaggtgaagctgtacgag
Phocle0.5  gaccaccgcatcgagatcctgagccacgacaaggactacaacaaggtgaagctgtacgag
phocle0.6  gaccaccgcatcgagatcctgagccacgacaaggactacaacaaggtgaagctgtacgag
Phocle0.7  gaccaccgcatcgagatcctgagccacgacaaggactacaacaaggtgaagctgtacgag
           ************************************************************
```

FIG. 15A

```
Phocle0.1  cacgccgtggcccgcaactccaccgacagcatggacgagctgtacaagggtggcagcggt
Phocle0.2  cacgccgtggcccgcaactccaccgacagcatggacgagctgtacaagggtggcagcggt
phocle0.3  cacgccgtggcccgcaactccaccgacagcatggacgagctgtacaagggtggcagcggt
phocle0.4  cacgccgtggcccgcaactccaccgacagcatggacgagctgtacaagggtggcagcggt
Phocle0.5  cacgccgtggcccgcaactccaccgacagcatggacgagctgtacaagggtggcagcggt
phocle0.6  cacgccgtggcccgcaactccaccgacagcatggacgagctgtacaagggtggcagcggt
Phocle0.7  cacgccgtggcccgcaactccaccgacagcatggacgagctgtacaagggtggcagcggt
           ************************************************************
Phocle0.1  ggcatggtgagcaagggcgaggagaccattatgagcgtgatcaagcctgacatgaagatc
Phocle0.2  ggcatggtgagcaagggcgaggagaccattacgagcgtgatcaagcctgacatgaagaac
phocle0.3  ggcatggtgagcaagggcgaggagaccattacgagcgtgatcaagcctgacatgaagaac
phocle0.4  ggcatggtgagcaagggcgaggagaccattacgagcgtgatcaagcctgacatgaagaac
Phocle0.5  ggcatggtgagcaagggcgaggagaccattacgagcgtgatcaagcctgacatgaagaac
phocle0.6  ggcatggtgagcaagggcgaggagaccattacgagcgtgatcaagcctgacatgaagaac
Phocle0.7  ggcatggtgagcaagggcgaggagaccattacaagcgtgatcaagcctgacatgaagaac
           *******************************..************************ *
Phocle0.1  aagctgcgcatggagggcaacgtgaacggccacgccttcgtgatcgagggcgagggcagc
Phocle0.2  aagctgcgcatggagggcaacgtgaacggccacgccttcgtgatcgagggcgagggcagc
phocle0.3  aagctgcgcatggagggcaacgtgaacggccacgccttcgtgatcgagggcgagggcagc
phocle0.4  aagctgcgcatggagggcaacgtgaacggccacgccttcgtgatcgagggcgagggcagc
Phocle0.5  aagctgcgcatggagggcaacgtgaacggccacgccttcgtgatcgagggcgagggcagc
phocle0.6  aagctgcgcatggagggcaacgtgaacggccacgccttcgtgatcgagggcgagggcagc
Phocle0.7  aagctgcgcatggagggcaacgtgaacggccacgccttcgtgatcgagggcgagggcagc
           ************************************************************
Phocle0.1  ggcaagcccttcgagggcatccagacgattgatttggaggtgaaggagggcgccccgctg
Phocle0.2  ggcaagcccttcgagggcatccagacgattgatttggaggtgaaggagggcgccccgctg
phocle0.3  ggcaagcccttcgagggcatccagacgattgatttggaggtgaaggagggcgccccgctg
phocle0.4  ggcaagcccttcgagggcatccagacgattgatttggaggtgaaggagggcgccccgctg
Phocle0.5  ggcaagcccttcgagggcatccagacgattgatttggaggtgaaggagggcgccccgctg
phocle0.6  ggcaagcccttcgagggcatccagacgattgatttggaggtgaaggagggcgccccgctg
Phocle0.7  ggcaagcccttcgagggcatccagacgattgatttggaggtgaaggagggcgccccgctg
           ************************************************************
Phocle0.1  cccttcgcctacgacatcctgaccaccgccttccactacggcaaccgcgtgttcaccaag
Phocle0.2  cccttcgcctacgacatcctgaccaccgccttccactacggcaaccgcgtgttcaccaag
phocle0.3  cccttcgcctacgacatcctgaccaccgccttccactacggcaaccgcgtgttcaccaag
phocle0.4  cccttcgcctacgacatcctgaccaccgccttccactacggcaaccgcgtgttcaccaag
Phocle0.5  cccttcgcctacgacatcctgaccaccgccttccactacggcaaccgcgtgttcaccaag
phocle0.6  cccttcgcctacgacatcctgaccaccgccttccactacggcaaccgcgtgttcaccaag
Phocle0.7  cccttcgcctacgacatcctgaccaccgccttccactacggcaaccgcgtgttcaccaag
           ************************************************************
Phocle0.1  tacccacggtaa
Phocle0.2  tacccacggtaa
phocle0.3  tacccacggtaa
phocle0.4  tacccacggtaa
Phocle0.5  tacccacggtaa
phocle0.6  tacccacggtaa
Phocle0.7  tacccacggtaa
           ************
```

FIG. 15B

```
phocle0.1  MVIPDYFKQSFPEGYSWERSMTYEDGGICIATNDITMEEDSFINKIHFKGTNFPPNGPVM
phocle0.2  MVIPDYFKQSFPEGYSWERSMTYEDGGICIATNDITMEEDSFINKIHFKGTNFPPNGPVM
phocle0.3  MVIPDYFKQSFPEGYSWERSMTYEDGGICIATNDITMEEDSFINKIHFKGTNFPPNGPVM
phocle0.4  MVIPDYFKQSFPEGYSWERSMTYEDGGICIATNDITMEEDSFINKIHFKGTNFPPNGPVM
phocle0.5  MVIPDYFKQSFPEGYSWERSMTYEDGGICIATNDITMEGDSFINKIHFKGTNFPPNGPVM
phocle0.6  MVIPDYFKQSFPEGYSWERSMTYEDGGICIATNDITMEGDSFINKIHFKGTNFPPNGPVM
phocle0.7  MVIPDYFKQSFPEGYSWERSMTYEDGGICIATNDITMEGDSFINKIHFKGTNFPPNGPVM
           ******************************** ********************
phocle0.1  QKRTVGWEVSTEKMYVRDGVLKGDVKMKLLLKGGSHYRCDFRTTYKVKQKAVKLPDYHFV
phocle0.2  QKRTVGWEVSTEKMYVRDGVLKGDVKMKLLLKGGSHYRCDFRTTYKVKQKAVKLPDYHFV
phocle0.3  QKRTVGWEVSTEKMYVRDGVLKGDVKMKLLLKGGSHYRCDYRTTYKVKQKAVKLPDYHFV
phocle0.4  QKRTVGWEVSTEKMYVRDGVLKGDVKMKLLLKGGGHYRCDYRTTYKVKQKAVKLPDYHFV
phocle0.5  QKRTVGWEASTEKMYVRDGVLKGDVKMKLLLKGGGHYRCDYRTTYKVKQKAVKLPDSHFV
phocle0.6  QKRTVGWEASTEKMYERDGVLKGDVKMKLLLKGGGHYRCDYRTTYKVKQKAVKLPDYHFV
phocle0.7  QKRTVGWEASTEKMYERDGVLKGDVKMKLLLKGGGHYRCDYRTTYKVKQKPVKLPDYHFV
           ********.****** ******************.*****:*********.***** ***
phocle0.1  DHRIEILSHDKDYNKVKLYEHAVARNSTDSMDELYKGGSGGMVSKGEETIMSVIKPDMKI
phocle0.2  DHRIEILSHDKDYNKVKLYEHAVARNSTDSMDELYKGGSGGMVSKGEETITSVIKPDMKN
phocle0.3  DHRIEILSHDKDYNKVKLYEHAVARNSTDSMDELYKGGSGGMVSKGEETITSVIKPDMKN
phocle0.4  DHRIEILSHDKDYNKVKLYEHAVARNSTDSMDELYKGGSGGMVSKGEETITSVIKPDMKN
phocle0.5  DHRIEILSHDKDYNKVKLYEHAVARNSTDSMDELYKGGSGGMVSKGEETITSVIKPDMKN
phocle0.6  DHRIEILSHDKDYNKVKLYEHAVARNSTDSMDELYKGGSGGMVSKGEETITSVIKPDMKN
phocle0.7  DHRIEILSHDKDYNKVKLYEHAVARNSTDSMDELYKGGSGGMVSKGEETITSVIKPDMKN
           ********************************************** ********
phocle0.1  KLRMEGNVNGHAFVIEGEGSGKPFEGIQTIDLEVKEGAPLPFAYDILTTAFHYGNRVFTK
phocle0.2  KLRMEGNVNGHAFVIEGEGSGKPFEGIQTIDLEVKEGAPLPFAYDILTTAFHYGNRVFTK
phocle0.3  KLRMEGNVNGHAFVIEGEGSGKPFEGIQTIDLEVKEGAPLPFAYDILTTAFHYGNRVFTK
phocle0.4  KLRMEGNVNGHAFVIEGEGSGKPFEGIQTIDLEVKEGAPLPFAYDILTTAFHYGNRVFTK
phocle0.5  KLRMEGNVNGHAFVIEGEGSGKPFEGIQTIDLEVKEGAPLPFAYDILTTAFHYGNRVFTK
phocle0.6  KLRMEGNVNGHAFVIEGEGSGKPFEGIQTIDLEVKEGAPLPFAYDILTTAFHYGNRVFTK
phocle0.7  KLRMEGNVNGHAFVIEGEGSGKPFEGIQTIDLEVKEGAPLPFAYDILTTAFHYGNRVFTK
           ************************************************************
phocle0.1  YPR
phocle0.2  YPR
phocle0.3  YPR
phocle0.4  YPR
phocle0.5  YPR
phocle0.6  YPR
phocle0.7  YPR
           ***
```

FIG. 16

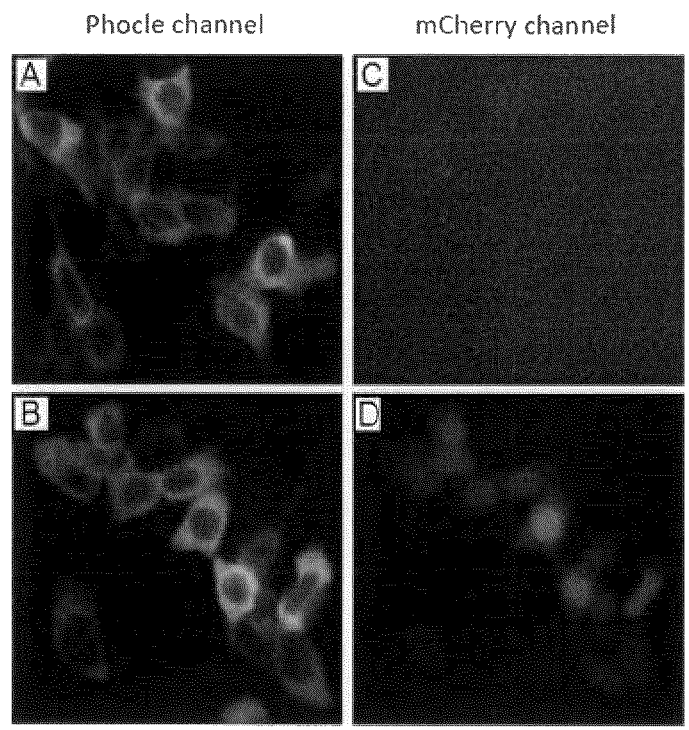
FIGS. 17A-D
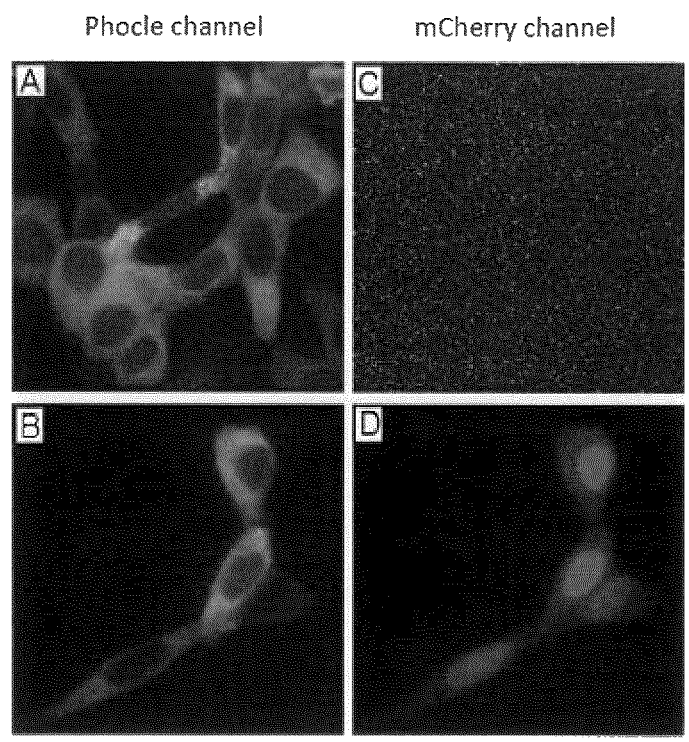
FIGS. 18A-D

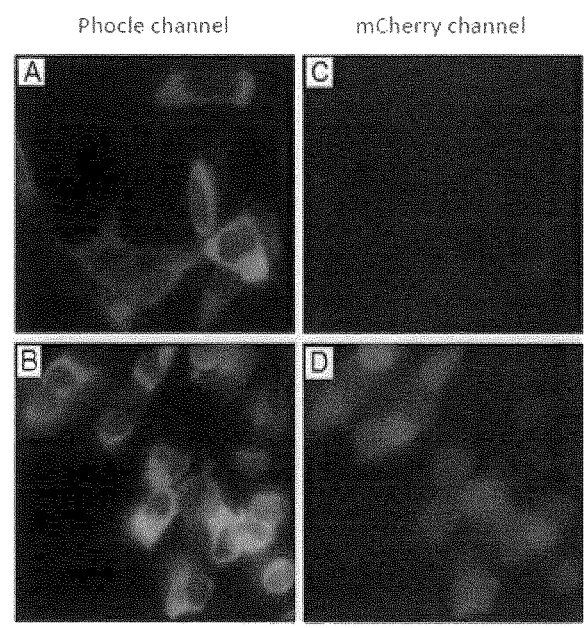
FIGS. 19A-D
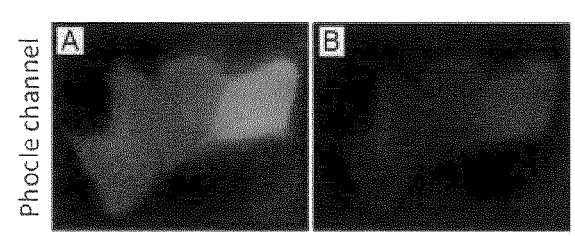
FIGS. 20A-B
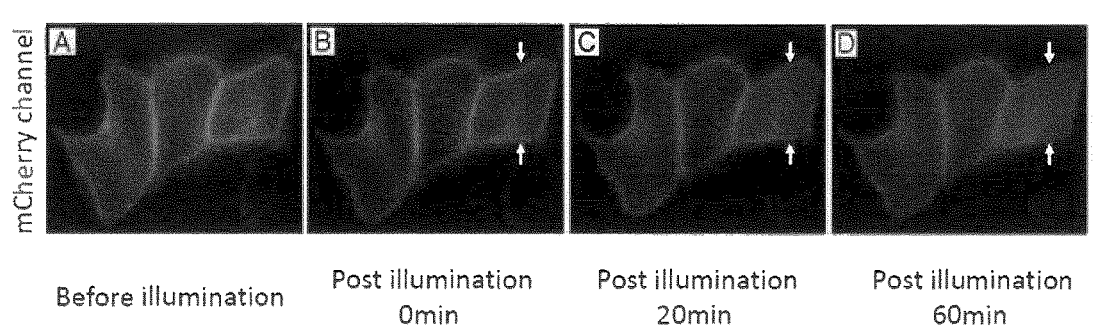
FIGS. 21A-D

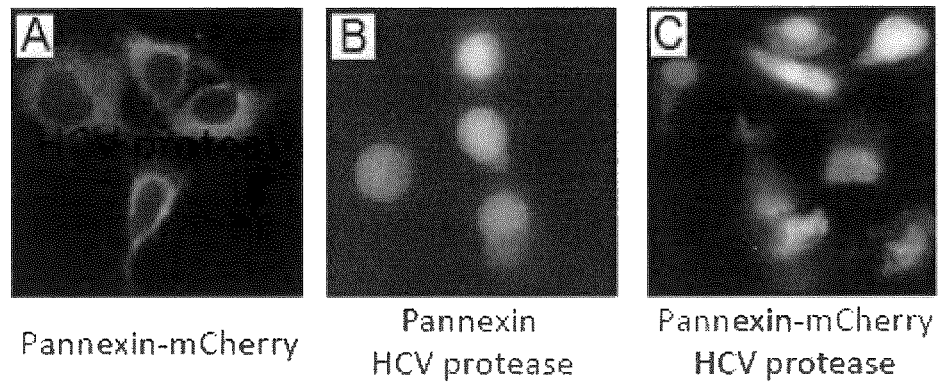
Pannexin-mCherry    Pannexin HCV protease    Pannexin-mCherry HCV protease
FIGS. 24A-C
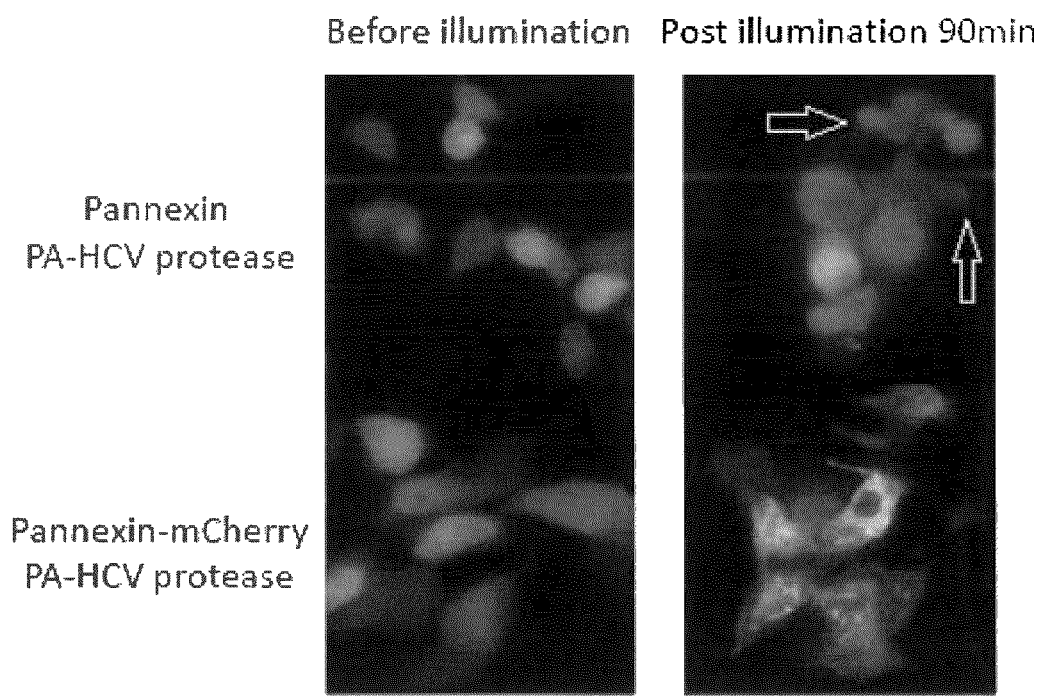
FIG. 25

SEQUENCE LISTING

<160> NUMBER OF SEQ ID NOS: 17

<210> SEQ ID NO 1
<211> LENGTH: 732
<212> TYPE: DNA
<213> ORGANISM: Artificial Sequence
<220> FEATURE:
<223> OTHER INFORMATION: PhoCle0.1

<400> SEQUENCE: 1
atggtgatcc ctgactactt caagcagagc ttccccgagg gctacagctg ggagcgcagc    60

```
atgacctacg aggacggcgg catctgcatc gccaccaacg acatcacaat ggaggaggac    120
agcttcatca acaagatcca cttcaagggc acgaacttcc ccccaacgg ccccgtgatg     180 cagaagagga ccgtgggctg ggaggtcagc accgagaaga tgtacgtgcg cgacggcgtg    240
ctgaagggcg acgtgaagat gaagctgctg ctgaagggcg gcagccacta tcgctgcgac    300
ttccgcacca cctacaaggt caagcagaag gccgtaaagc tgcccgacta ccacttcgtg    360
gaccaccgca tcgagatcct gagccacgac aaggactaca acaaggtgaa gctgtacgag    420
cacgccgtgg cccgcaactc caccgacagc atggacgagc tgtacaaggg tggcagcggt    480
ggcatggtga gcaagggcga ggagaccatt atgagcgtga tcaagcctga catgaagatc    540
aagctgcgca tggagggcaa cgtgaacggc cacgccttcg tgatcgaggg cgagggcagc    600
ggcaagccct tcgagggcat ccagacgatt gatttggagg tgaaggaggg cgccccgctg    660
cccttcgcct acgacatcct gaccaccgcc ttccactacg gcaaccgcgt gttcaccaag    720
tacccacggt aa                                                         732
```

<210> SEQ ID NO 2
<211> LENGTH: 243
<212> TYPE: PRT
<213> ORGANISM: Artificial Sequence
<220> FEATURE:
<223> OTHER INFORMATION: PhoCle0.1

<400> SEQUENCE: 2

```
Met Val Ile Pro Asp Tyr Phe Lys Gln Ser Phe Pro Glu Gly Tyr Ser
1               5                   10                  15

Trp Glu Arg Ser Met Thr Tyr Glu Asp Gly Gly Ile Cys Ile Ala Thr
            20                  25                  30

Asn Asp Ile Thr Met Glu Glu Asp Ser Phe Ile Asn Lys Ile His Phe
        35                  40                  45

Lys Gly Thr Asn Phe Pro Pro Asn Gly Pro Val Met Gln Lys Arg Thr
    50                  55                  60

Val Gly Trp Glu Val Ser Thr Glu Lys Met Tyr Val Arg Asp Gly Val
65                  70                  75                  80

Leu Lys Gly Asp Val Lys Met Lys Leu Leu Leu Lys Gly Gly Ser His
                85                  90                  95

Tyr Arg Cys Asp Phe Arg Thr Thr Tyr Lys Val Lys Gln Lys Ala Val
            100                 105                 110

Lys Leu Pro Asp Tyr His Phe Val Asp His Arg Ile Glu Ile Leu Ser
        115                 120                 125

His Asp Lys Asp Tyr Asn Lys Val Lys Leu Tyr Glu His Ala Val Ala
    130                 135                 140

Arg Asn Ser Thr Asp Ser Met Asp Glu Leu Tyr Lys Gly Gly Ser Gly
145                 150                 155                 160

Gly Met Val Ser Lys Gly Glu Glu Thr Ile Met Ser Val Ile Lys Pro
                165                 170                 175

Asp Met Lys Ile Lys Leu Arg Met Glu Gly Asn Val Asn Gly His Ala
            180                 185                 190

Phe Val Ile Glu Gly Glu Gly Ser Gly Lys Pro Phe Glu Gly Ile Gln
        195                 200                 205

Thr Ile Asp Leu Glu Val Lys Glu Gly Ala Pro Leu Pro Phe Ala Tyr
    210                 215                 220

Asp Ile Leu Thr Thr Ala Phe His Tyr Gly Asn Arg Val Phe Thr Lys
225                 230                 235                 240
```

Tyr Pro Arg

<210> SEQ ID NO 3
<211> LENGTH: 732
<212> TYPE: DNA
<213> ORGANISM: Artificial Sequence
<220> FEATURE:
<223> OTHER INFORMATION: PhoCle0.2

<400> SEQUENCE: 3

```
atggtgatcc ctgactactt caagcagagc ttccccgagg gctacagctg ggagcgcagc      60
atgacctacg aggacggcgg catctgcatc gccaccaacg acatcacaat ggaggaggac     120
agcttcatca acaagatcca cttcaagggc acgaacttcc ccccaacgg ccccgtgatg     180
cagaagagga ccgtgggctg ggaggtcagc accgagaaga tgtacgtgcg cgacggcgtg     240
ctgaagggcg acgtgaagat gaagctgctg ctgaagggcg gcagccacta tcgctgcgac     300
ttccgcacca cctacaaggt caagcagaag gccgtaaagc tgcccgacta ccacttcgtg     360
gaccaccgca tcgagatcct gagccacgac aaggactaca acaaggtgaa gctgtacgag     420
cacgccgtgg cccgcaactc caccgacagc atggacgagc tgtacaaggg tggcagcggt     480
ggcatggtga gcaagggcga ggagaccatt acgagcgtga tcaagcctga catgaagaac     540
aagctgcgca tggagggcaa cgtgaacggc cacgccttcg tgatcgaggg cgagggcagc     600
ggcaagccct tcgagggcat ccagacgatt gatttggagg tgaaggaggg cgccccgctg     660
cccttcgcct acgacatcct gaccaccgcc ttccactacg gcaaccgcgt gttcaccaag     720
tacccacggt aa                                                          732
```

<210> SEQ ID NO 4
<211> LENGTH: 243
<212> TYPE: PRT
<213> ORGANISM: Artificial Sequence
<220> FEATURE:
<223> OTHER INFORMATION: PhoCle0.2

<400> SEQUENCE: 4

```
Met Val Ile Pro Asp Tyr Phe Lys Gln Ser Phe Pro Glu Gly Tyr Ser
1               5                   10                  15

Trp Glu Arg Ser Met Thr Tyr Glu Asp Gly Gly Ile Cys Ile Ala Thr
            20                  25                  30

Asn Asp Ile Thr Met Glu Glu Asp Ser Phe Ile Asn Lys Ile His Phe
        35                  40                  45

Lys Gly Thr Asn Phe Pro Pro Asn Gly Pro Val Met Gln Lys Arg Thr
    50                  55                  60

Val Gly Trp Glu Val Ser Thr Glu Lys Met Tyr Val Arg Asp Gly Val
65                  70                  75                  80

Leu Lys Gly Asp Val Lys Met Lys Leu Leu Leu Lys Gly Gly Ser His
                85                  90                  95

Tyr Arg Cys Asp Phe Arg Thr Thr Tyr Lys Val Lys Gln Lys Ala Val
            100                 105                 110

Lys Leu Pro Asp Tyr His Phe Val Asp His Arg Ile Glu Ile Leu Ser
        115                 120                 125

His Asp Lys Asp Tyr Asn Lys Val Lys Leu Tyr Glu His Ala Val Ala
    130                 135                 140

Arg Asn Ser Thr Asp Ser Met Asp Glu Leu Tyr Lys Gly Gly Ser Gly
145                 150                 155                 160

Gly Met Val Ser Lys Gly Glu Glu Thr Ile Thr Ser Val Ile Lys Pro
```

```
                    165                 170                 175
Asp Met Lys Asn Lys Leu Arg Met Glu Gly Asn Val Asn Gly His Ala
                180                 185                 190

Phe Val Ile Glu Gly Glu Gly Ser Gly Lys Pro Phe Glu Gly Ile Gln
        195                 200                 205

Thr Ile Asp Leu Glu Val Lys Glu Gly Ala Pro Leu Pro Phe Ala Tyr
    210                 215                 220

Asp Ile Leu Thr Thr Ala Phe His Tyr Gly Asn Arg Val Phe Thr Lys
225                 230                 235                 240

Tyr Pro Arg

<210> SEQ ID NO 5
<211> LENGTH: 732
<212> TYPE: DNA
<213> ORGANISM: Artificial Sequence
<220> FEATURE:
<223> OTHER INFORMATION: PhoCle0.3

<400> SEQUENCE: 5
atggtgatcc ctgactactt caagcagagc ttccccgagg gctacagctg ggagcgcagc      60
atgacctacg aggacggcgg catctgcatc gccaccaacg acatcacaat ggaggaggac     120
agcttcatca acaagatcca cttcaagggc acgaacttcc ccccaacgg ccccgtgatg     180 cagaagagga ccgtgggctg ggaggtcagc accgagaaga tgtacgtgcg cgacggcgtg     240
ctgaagggcg acgtgaagat gaagctgctg ctgaagggcg gcagccacta cgctgcgac     300 taccgcacca cctacaaggt caagcagaag gccgtaaagc tgcccgacta ccacttcgtg     360
gaccaccgca tcgagatcct gagccacgac aaggactaca acaaggtgaa gctgtacgag     420
cacgccgtgg cccgcaactc caccgacagc atggacgagc tgtacaaggg tggcagcggt     480
ggcatggtga gcaagggcga ggagaccatt acgagcgtga tcaagcctga catgaagaac     540
aagctgcgca tggagggcaa cgtgaacggc cacgccttcg tgatcgaggg cgagggcagc     600
ggcaagccct tcgagggcat ccagacgatt gatttggagg tgaaggaggg cgccccgctg     660
cccttcgcct acgacatcct gaccaccgcc ttccactacg gcaaccgcgt gttcaccaag     720
tacccacggt aa                                                         732

<210> SEQ ID NO 6
<211> LENGTH: 243
<212> TYPE: PRT
<213> ORGANISM: Artificial Sequence
<220> FEATURE:
<223> OTHER INFORMATION: PhoCle0.3

<400> SEQUENCE: 6

Met Val Ile Pro Asp Tyr Phe Lys Gln Ser Phe Pro Glu Gly Tyr Ser
1               5                   10                  15

Trp Glu Arg Ser Met Thr Tyr Glu Asp Gly Gly Ile Cys Ile Ala Thr
            20                  25                  30

Asn Asp Ile Thr Met Glu Glu Asp Ser Phe Ile Asn Lys Ile His Phe
        35                  40                  45

Lys Gly Thr Asn Phe Pro Pro Asn Gly Pro Val Met Gln Lys Arg Thr
    50                  55                  60

Val Gly Trp Glu Val Ser Thr Glu Lys Met Tyr Val Arg Asp Gly Val
65                  70                  75                  80

Leu Lys Gly Asp Val Lys Met Lys Leu Leu Leu Lys Gly Gly Ser His
                85                  90                  95
```

Tyr Arg Cys Asp Tyr Arg Thr Thr Tyr Lys Val Lys Gln Lys Ala Val
                100                 105                 110

Lys Leu Pro Asp Tyr His Phe Val Asp His Arg Ile Glu Ile Leu Ser
            115                 120                 125

His Asp Lys Asp Tyr Asn Lys Val Lys Leu Tyr Glu His Ala Val Ala
130                 135                 140

Arg Asn Ser Thr Asp Ser Met Asp Glu Leu Tyr Lys Gly Gly Ser Gly
145                 150                 155                 160

Gly Met Val Ser Lys Gly Glu Glu Thr Ile Thr Ser Val Ile Lys Pro
                165                 170                 175

Asp Met Lys Asn Lys Leu Arg Met Glu Gly Asn Val Asn Gly His Ala
            180                 185                 190

Phe Val Ile Glu Gly Glu Gly Ser Gly Lys Pro Phe Glu Gly Ile Gln
        195                 200                 205

Thr Ile Asp Leu Glu Val Lys Glu Gly Ala Pro Leu Pro Phe Ala Tyr
    210                 215                 220

Asp Ile Leu Thr Thr Ala Phe His Tyr Gly Asn Arg Val Phe Thr Lys
225                 230                 235                 240

Tyr Pro Arg

<210> SEQ ID NO 7
<211> LENGTH: 732
<212> TYPE: DNA
<213> ORGANISM: Artificial Sequence
<220> FEATURE:
<223> OTHER INFORMATION: PhoCle0.4

<400> SEQUENCE: 7

```
atggtgatcc ctgactactt caagcagagc ttccccgagg gctacagctg ggagcgcagc      60
atgacctacg aggacggcgg catctgcatc gccaccaacg acatcacaat ggaggaggac     120
agcttcatca acaagatcca cttcaagggc acgaacttcc ccccaacgg ccccgtgatg     180
cagaagagga ccgtgggctg ggaggtcagc accgagaaga tgtacgtgcg cgacggcgtg     240
ctgaagggcg acgtgaagat gaagctgctg ctgaagggcg gcggccacta tcgctgcgac     300
taccgcacca cctacaaggt caagcagaag gccgtaaagc tgcccgacta ccacttcgtg     360
gaccaccgca tcgagatcct gagccacgac aaggactaca acaaggtgaa gctgtacgag     420
cacgccgtgg cccgcaactc caccgacagc atggacgagc tgtacaaggg tggcagcggt     480
ggcatggtga gcaagggcga ggagaccatt acgagcgtga tcaagcctga catgaagaac     540
aagctgcgca tggagggcaa cgtgaacggc cacgccttcg tgatcgaggg cgagggcagc     600
ggcaagccct cgagggcat ccagacgatt gatttggagg tgaaggaggg cgccccgctg     660
cccttcgcct acgacatcct gaccaccgcc ttccactacg caaccgcgt gttcaccaag     720
tacccacggt aa                                                        732
```

<210> SEQ ID NO 8
<211> LENGTH: 243
<212> TYPE: PRT
<213> ORGANISM: Artificial Sequence
<220> FEATURE:
<223> OTHER INFORMATION: PhoCle0.4

<400> SEQUENCE: 8

Met Val Ile Pro Asp Tyr Phe Lys Gln Ser Phe Pro Glu Gly Tyr Ser
1               5                   10                  15

Trp Glu Arg Ser Met Thr Tyr Glu Asp Gly Gly Ile Cys Ile Ala Thr
            20                  25                  30

Asn Asp Ile Thr Met Glu Glu Asp Ser Phe Ile Asn Lys Ile His Phe
            35                  40                  45

Lys Gly Thr Asn Phe Pro Pro Asn Gly Pro Val Met Gln Lys Arg Thr
        50                  55                  60

Val Gly Trp Glu Val Ser Thr Glu Lys Met Tyr Val Arg Asp Gly Val
65                  70                  75                  80

Leu Lys Gly Asp Val Lys Met Lys Leu Leu Leu Lys Gly Gly His
                85                  90                  95

Tyr Arg Cys Asp Tyr Arg Thr Thr Tyr Lys Val Lys Gln Lys Ala Val
            100                 105                 110

Lys Leu Pro Asp Tyr His Phe Val Asp His Arg Ile Glu Ile Leu Ser
            115                 120                 125

His Asp Lys Asp Tyr Asn Lys Val Lys Leu Tyr Glu His Ala Val Ala
        130                 135                 140

Arg Asn Ser Thr Asp Ser Met Asp Glu Leu Tyr Lys Gly Gly Ser Gly
145                 150                 155                 160

Gly Met Val Ser Lys Gly Glu Glu Thr Ile Thr Ser Val Ile Lys Pro
            165                 170                 175

Asp Met Lys Asn Lys Leu Arg Met Glu Gly Asn Val Asn Gly His Ala
            180                 185                 190

Phe Val Ile Glu Gly Glu Gly Ser Gly Lys Pro Phe Glu Gly Ile Gln
        195                 200                 205

Thr Ile Asp Leu Glu Val Lys Glu Gly Ala Pro Leu Pro Phe Ala Tyr
210                 215                 220

Asp Ile Leu Thr Thr Ala Phe His Tyr Gly Asn Arg Val Phe Thr Lys
225                 230                 235                 240

Tyr Pro Arg

<210> SEQ ID NO 9
<211> LENGTH: 732
<212> TYPE: DNA
<213> ORGANISM: Artificial Sequence
<220> FEATURE:
<223> OTHER INFORMATION: PhoCle0.5

<400> SEQUENCE: 9
atggtgatcc ctgactactt caagcagagc ttccccgagg gctacagctg ggagcgcagc      60
atgacctacg aggacggcgg catctgcatc gccaccaacg acatcacaat ggaggggggac    120 agcttcatca acaagatcca cttcaagggc acgaacttcc cccccaacgg ccccgtgatg     180
cagaagagga ccgtgggctg ggaggccagc accgagaaga tgtacgtgcg cgacggcgtg     240
ctgaagggcg acgtgaagat gaagctgctg ctgaagggcg gcggccacta tcgctgcgac     300
taccgcacca cctacaaggt caagcagaag gccgtaaagc tgcccgactc ccacttcgtg     360
gaccaccgca tcgagatcct gagccacgac aaggactaca acaaggtgaa gctgtacgag     420
cacgccgtgg cccgcaactc caccgacagc atggacgagc tgtacaaggg tggcagcggt     480
ggcatggtga gcaagggcga ggagaccatt acgagcgtga tcaagcctga catgaagaac     540
aagctgcgca tggagggcaa cgtgaacggc cacgccttcg tgatcgaggg cgagggcagc     600
ggcaagccct tcgagggcat ccagacgatt gatttggagg tgaaggaggg cgccccgctg     660
cccttcgcct acgacatcct gaccaccgcc ttccactacg gcaaccgcgt gttcaccaag     720
tacccacggt aa                                                         732

<210> SEQ ID NO 10
<211> LENGTH: 243
<212> TYPE: PRT
<213> ORGANISM: Artificial Sequence
<220> FEATURE:
<223> OTHER INFORMATION: PhoCle0.5

<400> SEQUENCE: 10

```
Met Val Ile Pro Asp Tyr Phe Lys Gln Ser Phe Pro Glu Gly Tyr Ser
1               5                   10                  15

Trp Glu Arg Ser Met Thr Tyr Glu Asp Gly Gly Ile Cys Ile Ala Thr
            20                  25                  30

Asn Asp Ile Thr Met Glu Gly Asp Ser Phe Ile Asn Lys Ile His Phe
        35                  40                  45

Lys Gly Thr Asn Phe Pro Pro Asn Gly Pro Val Met Gln Lys Arg Thr
    50                  55                  60

Val Gly Trp Glu Ala Ser Thr Glu Lys Met Tyr Val Arg Asp Gly Val
65                  70                  75                  80

Leu Lys Gly Asp Val Lys Met Lys Leu Leu Leu Lys Gly Gly His
                85                  90                  95

Tyr Arg Cys Asp Tyr Arg Thr Thr Tyr Lys Val Lys Gln Lys Ala Val
                100                 105                 110

Lys Leu Pro Asp Ser His Phe Val Asp His Arg Ile Glu Ile Leu Ser
            115                 120                 125

His Asp Lys Asp Tyr Asn Lys Val Lys Leu Tyr Glu His Ala Val Ala
        130                 135                 140

Arg Asn Ser Thr Asp Ser Met Asp Glu Leu Tyr Lys Gly Gly Ser Gly
145                 150                 155                 160

Gly Met Val Ser Lys Gly Glu Glu Thr Ile Thr Ser Val Ile Lys Pro
                165                 170                 175

Asp Met Lys Asn Lys Leu Arg Met Glu Gly Asn Val Asn Gly His Ala
            180                 185                 190

Phe Val Ile Glu Gly Glu Gly Ser Gly Lys Pro Phe Glu Gly Ile Gln
        195                 200                 205

Thr Ile Asp Leu Glu Val Lys Glu Gly Ala Pro Leu Pro Phe Ala Tyr
    210                 215                 220

Asp Ile Leu Thr Thr Ala Phe His Tyr Gly Asn Arg Val Phe Thr Lys
225                 230                 235                 240

Tyr Pro Arg
```

<210> SEQ ID NO 11
<211> LENGTH: 732
<212> TYPE: DNA
<213> ORGANISM: Artificial Sequence
<220> FEATURE:
<223> OTHER INFORMATION: PhoCle0.6

<400> SEQUENCE: 11

```
atggtgatcc ctgactactt caagcagagc ttccccgagg gctacagctg ggagcgcagc     60
atgacctacg aggacggcgg catctgcatc gccaccaacg acatcacaat ggaggggggac    120 agcttcatca acaagatcca cttcaagggc acgaacttcc cccccaacgg ccccgtgatg    180
cagaagagga ccgtgggctg ggaggccagc accgagaaga tgtacgagcg cgacggcgtg    240
ctgaagggcg acgtgaagat gaagctgctg ctgaagggcg gcggccacta cgctgcgac     300 taccgcacca cctacaaggt caagcagaag gccgtaaagc tgcccgacta ccacttcgtg    360
```

```
gaccaccgca tcgagatcct gagccacgac aaggactaca acaaggtgaa gctgtacgag    420
cacgccgtgg cccgcaactc caccgacagc atgacgagc tgtacaaggg tggcagcggt    480
ggcatggtga gcaagggcga ggagaccatt acgagcgtga tcaagcctga catgaagaac    540
aagctgcgca tggagggcaa cgtgaacggc acgccttcg tgatcgaggg cgagggcagc    600
ggcaagccct cgagggcat ccagacgatt gatttggagg tgaaggaggg cgccccgctg    660
cccttcgcct acgacatcct gaccaccgcc ttccactacg caaccgcgt gttcaccaag    720 tacccacggt aa    732
```

```
<210> SEQ ID NO 12
<211> LENGTH: 243
<212> TYPE: PRT
<213> ORGANISM: Artificial Sequence
<220> FEATURE:
<223> OTHER INFORMATION: PhoCle0.6

<400> SEQUENCE: 12

Met Val Ile Pro Asp Tyr Phe Lys Gln Ser Phe Pro Glu Gly Tyr Ser
1               5                   10                  15

Trp Glu Arg Ser Met Thr Tyr Glu Asp Gly Gly Ile Cys Ile Ala Thr
            20                  25                  30

Asn Asp Ile Thr Met Glu Gly Asp Ser Phe Ile Asn Lys Ile His Phe
        35                  40                  45

Lys Gly Thr Asn Phe Pro Pro Asn Gly Pro Val Met Gln Lys Arg Thr
    50                  55                  60

Val Gly Trp Glu Ala Ser Thr Glu Lys Met Tyr Glu Arg Asp Gly Val
65                  70                  75                  80

Leu Lys Gly Asp Val Lys Met Lys Leu Leu Leu Lys Gly Gly His
                85                  90                  95

Tyr Arg Cys Asp Tyr Arg Thr Thr Tyr Lys Val Lys Gln Lys Ala Val
            100                 105                 110

Lys Leu Pro Asp Tyr His Phe Val Asp His Arg Ile Glu Ile Leu Ser
        115                 120                 125

His Asp Lys Asp Tyr Asn Lys Val Lys Leu Tyr Glu His Ala Val Ala
    130                 135                 140

Arg Asn Ser Thr Asp Ser Met Asp Glu Leu Tyr Lys Gly Gly Ser Gly
145                 150                 155                 160

Gly Met Val Ser Lys Gly Glu Glu Thr Ile Thr Ser Val Ile Lys Pro
                165                 170                 175

Asp Met Lys Asn Lys Leu Arg Met Glu Gly Asn Val Asn Gly His Ala
            180                 185                 190

Phe Val Ile Glu Gly Glu Gly Ser Gly Lys Pro Phe Glu Gly Ile Gln
        195                 200                 205

Thr Ile Asp Leu Glu Val Lys Glu Gly Ala Pro Leu Pro Phe Ala Tyr
    210                 215                 220

Asp Ile Leu Thr Thr Ala Phe His Tyr Gly Asn Arg Val Phe Thr Lys
225                 230                 235                 240

Tyr Pro Arg
```

```
<210> SEQ ID NO 13
<211> LENGTH: 732
<212> TYPE: DNA
<213> ORGANISM: Artificial Sequence
<220> FEATURE:
<223> OTHER INFORMATION: PhoCle0.7
```

<400> SEQUENCE: 13

```
atggtgatcc ctgactactt caagcagagc ttccccgagg gctacagctg ggagcgcagc      60
atgacctacg aggacggcgg catctgcatc gccaccaacg acatcacaat ggagggggac     120
agcttcatca acaagatcca cttcaagggc acgaacttcc ccccaacgg ccccgtgatg      180
cagaagagga ccgtgggctg ggaggccagc accgagaaga tgtacgagcg cgacggcgtg     240
ctgaagggcg acgtgaagat gaagctgctg ctgaagggcg gcggccacta tcgctgcgac     300
taccgcacca cctacaaggt caagcagaag cccgtaaagc tgcccgacta ccacttcgtg     360
gaccaccgca tcgagatcct gagccacgac aaggactaca acaaggtgaa gctgtacgag     420
cacgccgtgg cccgcaactc caccgacagc atggacgagc tgtacaaggg tggcagcggt     480
ggcatggtga gcaagggcga ggagaccatt acaagcgtga tcaagcctga catgaagaac     540
aagctgcgca tggagggcaa cgtgaacggc cacgccttcg tgatcgaggg cgagggcagc     600
ggcaagccct tcgagggcat ccagacgatt gatttggagg tgaaggaggg cgccccgctg     660
cccttcgcct acgacatcct gaccaccgcc ttccactacg gcaaccgcgt gttcaccaag     720
tacccacggt aa                                                          732
```

<210> SEQ ID NO 14
<211> LENGTH: 243
<212> TYPE: PRT
<213> ORGANISM: Artificial Sequence
<220> FEATURE:
<223> OTHER INFORMATION: PhoCle0.7

<400> SEQUENCE: 14

```
Met Val Ile Pro Asp Tyr Phe Lys Gln Ser Phe Pro Glu Gly Tyr Ser
  1               5                  10                  15

Trp Glu Arg Ser Met Thr Tyr Glu Asp Gly Gly Ile Cys Ile Ala Thr
             20                  25                  30

Asn Asp Ile Thr Met Glu Gly Asp Ser Phe Ile Asn Lys Ile His Phe
         35                  40                  45

Lys Gly Thr Asn Phe Pro Pro Asn Gly Pro Val Met Gln Lys Arg Thr
     50                  55                  60

Val Gly Trp Glu Ala Ser Thr Glu Lys Met Tyr Glu Arg Asp Gly Val
 65                  70                  75                  80

Leu Lys Gly Asp Val Lys Met Lys Leu Leu Leu Lys Gly Gly Gly His
                 85                  90                  95

Tyr Arg Cys Asp Tyr Arg Thr Thr Tyr Lys Val Lys Gln Lys Pro Val
            100                 105                 110

Lys Leu Pro Asp Tyr His Phe Val Asp His Arg Ile Glu Ile Leu Ser
        115                 120                 125

His Asp Lys Asp Tyr Asn Lys Val Lys Leu Tyr Glu His Ala Val Ala
    130                 135                 140

Arg Asn Ser Thr Asp Ser Met Asp Glu Leu Tyr Lys Gly Gly Ser Gly
145                 150                 155                 160

Gly Met Val Ser Lys Gly Glu Glu Thr Ile Thr Ser Val Ile Lys Pro
                165                 170                 175

Asp Met Lys Asn Lys Leu Arg Met Glu Gly Asn Val Asn Gly His Ala
            180                 185                 190

Phe Val Ile Glu Gly Glu Gly Ser Gly Lys Pro Phe Glu Gly Ile Gln
        195                 200                 205

Thr Ile Asp Leu Glu Val Lys Glu Gly Ala Pro Leu Pro Phe Ala Tyr
```

```
                    210                 215                 220

Asp Ile Leu Thr Thr Ala Phe His Tyr Gly Asn Arg Val Phe Thr Lys
225                 230                 235                 240

Tyr Pro Arg

<210> SEQ ID NO 15
<211> LENGTH: 714
<212> TYPE: DNA
<213> ORGANISM: Artificial Sequence
<220> FEATURE:
<223> OTHER INFORMATION: CpPhoCle
<220> FEATURE:
<221> NAME/KEY: misc_feature
<222> LOCATION: (246)..(247)
<223> OTHER INFORMATION: loop insertion always present between positions
      246 and 247
<220> FEATURE:
<221> NAME/KEY: misc_feature
<222> LOCATION: (715)..(715)
<223> OTHER INFORMATION: linker

<400> SEQUENCE: 15
atggtgagca agggcgagga gaccattacg agcgtgatca agcctgacat gaagaacaag      60
ctgcgcatgg agggcaacgt gaacggccac gccttcgtga tcgagggcga gggcagcggc     120
aagcccttcg agggcatcca gacgattgat ttggaggtga aggagggcgc cccgctgccc     180
ttcgcctacg acatcctgac caccgccttc cactacggca accgcgtgtt caccaagtac     240
ccacgtagta tccctgacta cttcaagcag agcttccccg agggctacag ctgggagcgc     300
agcatgacct acgaggacgg cggcatctgc atcgccacca cgacatcac aatggaggag     360 gacagcttca tcaacaagat ccacttcaag ggcacgaact ccccccccaa cggccccgtg     420
atgcagaaga ggaccgtggg ctgggaggtc agcaccgaga gatgtacgt gcgcgacggc     480 gtgctgaagg gcgacgtgaa gatgaagctg ctgctgaagg gcggcagcca ctatcgctgc     540
gacttccgca ccacctacaa ggtcaagcag aaggccgtaa agctgcccga ctaccacttc     600
gtggaccacc gcatcgagat cctgagccac gacaaggact acaacaaggt gaagctgtac     660
gagcacgccg tggcccgcaa ctccaccgac agcatggacg agctgtacaa gtaa           714

<210> SEQ ID NO 16
<211> LENGTH: 237
<212> TYPE: PRT
<213> ORGANISM: Artificial Sequence
<220> FEATURE:
<223> OTHER INFORMATION: CpPhoCle
<220> FEATURE:
<221> NAME/KEY: misc_feature
<222> LOCATION: (82)..(83)
<223> OTHER INFORMATION: loop insertion always present between positions
      82 and 83

<400> SEQUENCE: 16

Met Val Ser Lys Gly Glu Glu Thr Ile Thr Ser Val Ile Lys Pro Asp
1               5                   10                  15

Met Lys Asn Lys Leu Arg Met Glu Gly Asn Val Asn Gly His Ala Phe
            20                  25                  30

Val Ile Glu Gly Glu Gly Ser Gly Lys Pro Phe Glu Gly Ile Gln Thr
        35                  40                  45

Ile Asp Leu Glu Val Lys Glu Gly Ala Pro Leu Pro Phe Ala Tyr Asp
    50                  55                  60

Ile Leu Thr Thr Ala Phe His Tyr Gly Asn Arg Val Phe Thr Lys Tyr
65                  70                  75                  80
```

```
Pro Arg Ser Ile Pro Asp Tyr Phe Lys Gln Ser Phe Pro Glu Gly Tyr
                85                  90                  95

Ser Trp Glu Arg Ser Met Thr Tyr Glu Asp Gly Gly Ile Cys Ile Ala
            100                 105                 110

Thr Asn Asp Ile Thr Met Glu Glu Asp Ser Phe Ile Asn Lys Ile His
            115                 120                 125

Phe Lys Gly Thr Asn Phe Pro Pro Asn Gly Pro Val Met Gln Lys Arg
130                 135                 140

Thr Val Gly Trp Glu Val Ser Thr Glu Lys Met Tyr Val Arg Asp Gly
145                 150                 155                 160

Val Leu Lys Gly Asp Val Lys Met Lys Leu Leu Leu Lys Gly Gly Ser
                165                 170                 175

His Tyr Arg Cys Asp Phe Arg Thr Thr Tyr Lys Val Lys Gln Lys Ala
            180                 185                 190

Val Lys Leu Pro Asp Tyr His Phe Val Asp His Arg Ile Glu Ile Leu
            195                 200                 205

Ser His Asp Lys Asp Tyr Asn Lys Val Lys Leu Tyr Glu His Ala Val
210                 215                 220

Ala Arg Asn Ser Thr Asp Ser Met Asp Glu Leu Tyr Lys
225                 230                 235

<210> SEQ ID NO 17
<211> LENGTH: 237
<212> TYPE: PRT
<213> ORGANISM: Artificial Sequence
<220> FEATURE:
<223> OTHER INFORMATION: mMaple

<400> SEQUENCE: 17

Met Val Ser Lys Gly Glu Glu Thr Ile Met Ser Val Ile Lys Pro Asp
1               5                   10                  15

Met Lys Ile Lys Leu Arg Met Glu Gly Asn Val Asn Gly His Ala Phe
            20                  25                  30

Val Ile Glu Gly Glu Gly Ser Gly Lys Pro Phe Glu Gly Ile Gln Thr
        35                  40                  45

Ile Asp Leu Glu Val Lys Glu Gly Ala Pro Leu Pro Phe Ala Tyr Asp
50                  55                  60

Ile Leu Thr Thr Ala Phe His Tyr Gly Asn Arg Val Phe Thr Lys Tyr
65                  70                  75                  80

Pro Glu Asp Ile Pro Asp Tyr Phe Lys Gln Ser Phe Pro Glu Gly Tyr
                85                  90                  95

Ser Trp Glu Arg Ser Met Thr Tyr Glu Asp Gly Gly Ile Cys Ile Ala
            100                 105                 110

Thr Asn Asp Ile Thr Met Glu Glu Asp Ser Phe Ile Asn Lys Ile His
            115                 120                 125

Phe Lys Gly Thr Asn Phe Pro Pro Asn Gly Pro Val Met Gln Lys Arg
130                 135                 140

Thr Val Gly Trp Glu Val Ser Thr Glu Lys Met Tyr Val Arg Asp Gly
145                 150                 155                 160

Val Leu Lys Gly Asp Val Lys Met Lys Leu Leu Leu Lys Gly Gly Ser
                165                 170                 175

His Tyr Arg Cys Asp Phe Arg Thr Thr Tyr Lys Val Lys Gln Lys Ala
            180                 185                 190

Val Lys Leu Pro Asp Tyr His Phe Val Asp His Arg Ile Glu Ile Leu
            195                 200                 205
```

```
Ser His Asp Lys Asp Tyr Asn Lys Val Lys Leu Tyr Glu His Ala Val
    210                 215                 220
Ala Arg Asn Ser Thr Asp Ser Met Asp Glu Leu Tyr Lys
225                 230                 235
```

GENETICALLY ENCODED PHOTOCLEAVABLE PROTEINS

FIELD OF THE INVENTION

The present invention relates to proteins which are photocleavable and, upon photocleavage, spontaneously dissociate into two distinct fragments or release one end of an internal loop.

BACKGROUND OF THE INVENTION

Optogenetics refers to techniques involving the use of genetically encoded proteins, which fluoresce or change conformation upon absorption of visible light, as reporters or actuators respectively, of biological systems (Knöpfel et al., 2010; Alford et al., 2013). The prototypical optogenetic reporter is the *Aequorea victoria* green FP (GFP), while the prototypical optogenetic actuator is channelrhodopsin-2 (Chr2) from the algae *Chlamydomonas reinhardtii* (Boyden et al., 2005). GFP is a genetically encoded fluorophore that enables visualization of the localization and dynamics of chimeric fusion proteins in live cells (Tsien, 1998). ChR2 is a light activated channel that opens upon illumination, allowing cations to enter the cell which in turn causes a depolarization of the membrane potential (Nagel et al., 2003; Boyden et al., 2005; Fenno et al., 2011; Yizhar et al., 2011). These examples have inspired the development of variations to expand the range of optogenetic applications (Campbell and Davidson, 2010; Ibraheem and Campbell, 2010; Zhao et al., 2011; Mutoh et al., 2012; Jin et al., 2012; Chen et al., 2013; Hertel and Zhang, 2013; Wu et al., 2013).

For optogenetic actuators, there is a currently a limited toolbox of variants (Akerboom et al., 2013; Müller and Weber, 2013). There are several classes of optogenetic actuators. Opsin-based actuators are membrane-spanning channels that open and pass small ions in response to optical activation (Boyden et al., 2005; Zhang et al., 2007; Klare et al., 2008; Zhang et al., 2008; Airan et al., 2009; Berndt et al., 2009; Chow et al., 2010; Gunaydin et al., 2010; Knöpfel et al., 2010; Berndt et al., 2011; Fenno et al., 2011; Yizhar et al., 2011; Prigge et al., 2012; Karunarathne et al., 2013).

Allosteric-based actuators including BLUF, LOV, and PYP domains are typically small proteins (less than 140 amino acids) with a flavin adenine dinucleotide or flavin mononucleotide chromophore cofactor. Blue light illumination causes structural changes that unfold the C-terminal α-helix (Iseki et al., 2002; Schröder-Lang et al., 2007; Stierl et al., 2011; Christie et al., 2012). Attempts have been made to exploit the conformational change in these domains to modulate a desired genetically fused enzyme. Many of these efforts were inspired by the engineering of a photoactivatable hybrid between the GTPase Rac1 and a LOV domain (PA-Rac) (Wu et al., 2009). As Rac1 is involved in the regulation of cytoskeleton remodeling, localized illumination of a cell expressing PA-Rac stimulates cell migration in an experimentally controllable way. Replicating the success of PA-Rac with other enzymes has been challenging (Mills et al., 2011; Schierling and Pingoud, 2012). In the case of the LOV-luciferase hybrid, only about a 20% decrease in activity was ultimately achieved upon illumination (Hattori et al., 2013). Efforts have been made to use LOV domains for purposes other than enzyme control including caging of binding peptides (Lungu et al., 2012) and photo control of a protein degradation sequence (Renicke et al., 2013). Attempts to make such constructs have failed and provide only modest light dependent modulation (Strickland et al., 2010).

Oligomerization-based actuators are proteins which undergo light-dependent modulation of quaternary structure (Yazawa et al., 2009; Strickland et al., 2012; Zhou et al., 2012). Oligomerization-based actuators are the most diverse class of actuators, but also the one with the greatest redundancy in terms of functionality, and undergo a change in intermolecular interactions (i.e., formation or dissociation of homo- or heterodimers or higher order oligomers) upon illumination (Shimizu-Sato et al., 2002; Levskaya et al., 2009; Yazawa et al., 2009; Kennedy et al., 2010; Toettcher et al., 2011; Christie et al., 2012; Idevall-Hagren et al., 2012; Strickland et al., 2012; Wu et al., 2012; Zhou et al., 2012; Bugaj et al., 2013; Kakumoto and Nakata, 2013; Pathak et al., 2013; Yang et al., 2013). As optogenetic actuators, light-activated oligomerizers are generally restricted to being applied for either reconstitution of split proteins or perturbation of protein subcellular localization.

An ideal optogenetic tool is one in which all components, including the chromophore, are proteinaceous. The prior art actuators described above require chromophore cofactors that are normally present in cells or can be introduced into cells either by incubation in solution (Levskaya et al., 2009) or introduction of the required biosynthetic genes (Müller et al., 2013). This requirement for chromophore cofactors is not problematic in many in vitro applications, but for in vivo applications the accompanying depletion of cellular cofactors or the need for systematic delivery presents complications. Oligomerization-based actuators that are fully proteinaceous avoid these problems and are better suited to in vivo applications. A fully proteinaceous actuator, UVR8, uses its intrinsic tryptophan residues to absorb UV light and has been exploited as both a light dissociable homodimer and a light induced heterodimer with COP1 (Rizzini et al., 2011; Crefcoeur et al., 2013). One recent application of the UVR8-COP1 system was the photocontrol of protein secretion by dissociation of oligomerized vesicular stomatitis virus glycoprotein in dissociated neurons (Chen et al., 2013). However, the UVR8 system requires high energy UV light, making it unsuitable for in vivo applications. The Dronpa FP-based reversible tetramer dissociation system appears promising (Zhou et al., 2012). As a homologue of *Aequorea* GFP, Dronpa autogenically forms a visible wavelength chromophore within the protected interior of its β-barrel structure. A light-induced change in the conformation of the chromophore triggers structural changes in the β-barrel that lead to dissociation of the Dronpa tetramer (Mizuno et al., 2008). This approach has been used for reversible release from the plasma membrane and caging of proteins due to a combination of clustering, structural perturbation, and active site obstruction. Implementing the Dronpa-based caging of enzymes is challenging since successful designs are largely based on trial and error, and it is difficult to fully turn proteins off in the dark or oligomerized state.

Thus, there exists a need in the art for the continued development of fluorescent proteins for use in scientific applications which may mitigate the technical limitations of the prior art.

SUMMARY OF THE INVENTION

The present invention relates to proteins which are photocleavable and, upon photocleavage, spontaneously dissociate into fragments or release an end of an internal loop.

In one aspect, the invention comprises a photocleavable genetically encoded protein comprising a His-Tyr-Gly chromophore, wherein said protein spontaneously dissociates into at least two fragments, or releases one end of a loop insertion, following photocleavage. In one embodiment, the photocleavable protein of claim 1 changes from green to red fluorescence to a non-fluorescent state upon photocleavage, and has a tertiary structure comprising an α-helix comprises the chromophore His-Tyr-Gly within a β-barrel comprising a β-sheet, the protein comprises a sequence break between the α-helix and a β-sheet, the sequence break consisting of a C-terminus and a N-terminus or a loop insertion comprising a functional polypeptide sequence.

In one embodiment, the sequence break comprises a loop insertion comprising a functional polypeptide sequence.

In another aspect, the invention comprises nucleic acid sequences which encode a photocleavable protein of the present invention, and recombinant expression vectors comprising nucleic acid sequences which encode such photocleavable proteins, operably linked with transcriptional and translational regulatory regions or sequences to provide for expression of the nucleic acid in a host cell. The vector may be used to transform an isolated host cell. The invention may comprise a transgenic animal comprising a nucleic acid which encodes a photocleavable protein.

In another aspect, the invention may comprise a method of engineering a photocleavable protein comprising a chromophore His-Tyr-Gly, which spontaneously dissociates into two or more fragments, or releases one end of a loop insertion, following photocleavage, the method comprising the steps of:

(a) generating a library of circularly permuted variants of a fluorescent protein containing the His-Tyr-Gly-derived chromophore;

(b) selecting those variants which photocleave and which display a green to red to non-fluorescent state upon photocleavage; and (c) further selecting those variants which display fragment dissociation or loop release.

The selected variants of step (b) and/or step (c) may undergo directed evolution and/or additional circular permuting to identify or obtain additional variants of the selected variants.

In another aspect, the invention may comprise methods of localizing a protein within a cell comprising the step of providing a photocleavable genetically encoded protein comprising a His-Tyr-Gly chromophore, wherein said protein spontaneously dissociates into at least two fragments following photocleavage, wherein one or more fragments comprises a localization tag or an exclusion tag, and photo cleaving the protein.

In another aspect, the invention may comprise methods of enzyme activation comprising the step of providing a photocleavable genetically encoded protein construct comprising a His-Tyr-Gly chromophore and the enzyme and an enzyme inhibitor, wherein said protein construct spontaneously dissociates into at least two fragments following photocleavage, wherein a first fragment comprises the enzyme, and a second fragment comprises the inhibitor.

In another aspect, the invention may comprise methods of patterning a biocompatible surface using an immobilized protein of interest comprising the steps of (a) providing a photocleavable genetically encoded protein comprising a His-Tyr-Gly chromophore and a sequence break consisting of a C-terminus and a N-terminus wherein said protein spontaneously dissociates into at least two fragments following photocleavage, or a sequence break consisting of a loop insertion which releases one end of the loop upon photocleavage, wherein one fragment comprises a surface binding moiety, and the other fragment comprises a protein of interest binding moiety, or the released end of the loop comprises a protein of interest binding moeity;

(b) masking a portion of the biocompatible surface and illuminating with a photocleaving light; and (c) applying the protein of interest to the biocompatible surface.

In another aspect, the invention may comprise methods of uncaging a functional polypeptide, comprising the steps of providing a genetically encoded photocleavable protein comprising a His-Tyr-Gly chromophore and a sequence break consisting of a loop insertion comprising the functional polypeptide, and photocleaving the protein such that one end of the loop insertion is released, thereby uncaging the functional polypeptide.

In another aspect, the invention may comprise methods of purifying a protein of interest using a purification substrate having an affinity tag, comprising the step of providing a genetically encoded photocleavable protein comprising a His-Tyr-Gly chromophore and a sequence break consisting of a C-terminus and a N-terminus, wherein the protein spontaneously dissociates into two fragments following photocleavage, wherein one fragment comprises an affinity tag which specifically binds to the substrate affinity tag, and the other fragment comprises the protein of interest.

Additional aspects and advantages of the present invention will be apparent in view of the description, which follows. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The invention will now be described by way of an exemplary embodiment with reference to the accompanying simplified, diagrammatic, not-to-scale drawings:

FIG. 4 is a sequence alignment of PhoCle variants with the progenitor protein mMaple.

FIG. 14A shows the cpPhoCle nucleotide sequence (SEQ ID NO: 15 with a non-functional loop insertion), and FIG. 14B shows the cpPhoCle amino acid sequence (SEQ ID NO: 16 with a non-functional loop insertion). The non-functional loop insertions are highlighted.

FIGS. 15A and 15B show an alignment of the nucleic acid sequences of PhoCle0.1 (SEQ ID NO: 1), PhoCle0.2 (SEQ ID NO: 3), PhoCle0.3 (SEQ ID NO: 5), PhoCle0.4 (SEQ ID NO: 7), PhoCle0.5 (SEQ ID NO: 9), PhoCle0.6 (SEQ ID NO: 11), and PhoCle0.7 (SEQ ID NO: 13).

FIG. 16 is an alignment of the amino acid sequences of PhoCle0.1 (SEQ ID NO: 2), PhoCle0.2 (SEQ ID NO: 4), PhoCle0.3 (SEQ ID NO: 6), PhoCle0.4 (SEQ ID NO: 8), PhoCle0.5 (SEQ ID NO: 10), PhoCle0.6 (SEQ ID NO: 12), and PhoCle0.7 (SEQ ID NO: 14).

FIGS. 17A-D show green (FIGS. 17A-B) and red (FIGS. 17C-D) fluorescence images of cells after transfection with pCAG ER$^{T2}$-PhoCle-Gal4-vp16-PhoCle-ER$^{T2}$ carrying pUAS-mCherry-NLS. Illumination was applied to the cells in FIGS. 17B and D.

FIGS. 18A-D show green (FIGS. 18A-B) and red (FIGS. 18C-D) fluorescence images of cells after transfection with pCAG ER$^{T2}$-PhoCle-Gal4-vp16-PhoCle-ER$^{T2}$ carrying pUAS-mCherry-NLS. Illumination was applied to the cells in FIGS. 18B and D.

FIGS. 19A-D show green (FIGS. 19A-B) and red (FIGS. 19C-D) fluorescence images of cells after transfection with ER$^{T2}$-PhoCle-Cre-PhoCle-ER$^{T2}$ carrying double floxed mCherry. Illumination was applied to the cells in FIGS. 19B and D.

FIGS. 20A-B show PhoCle green channel fluorescence images of the cytoplasm of a cell before (FIG. 20A) and after illumination (FIG. 20B).

FIGS. 21A-D show mCherry red channel images before illumination (FIG. 21A) and 0 min, 20 mins, and 60 mins after illumination (FIGS. 21B-D).

FIGS. 24A-C show mammalian cells co-transfected with pannexin-mCherry (FIG. 24A); pannexin and HCV protease (FIG. 24B); and pannexin-mCherry and HCV protease (FIG. 24C).

FIG. 25 shows mammalian cells co-transfected with pannexin and PA-HCV protease, and pannexin-mCherry and PA-HCV protease before and 90 mins after illumination.

DETAILED DESCRIPTION OF PREFERRED EMBODIMENTS

Figure 1:
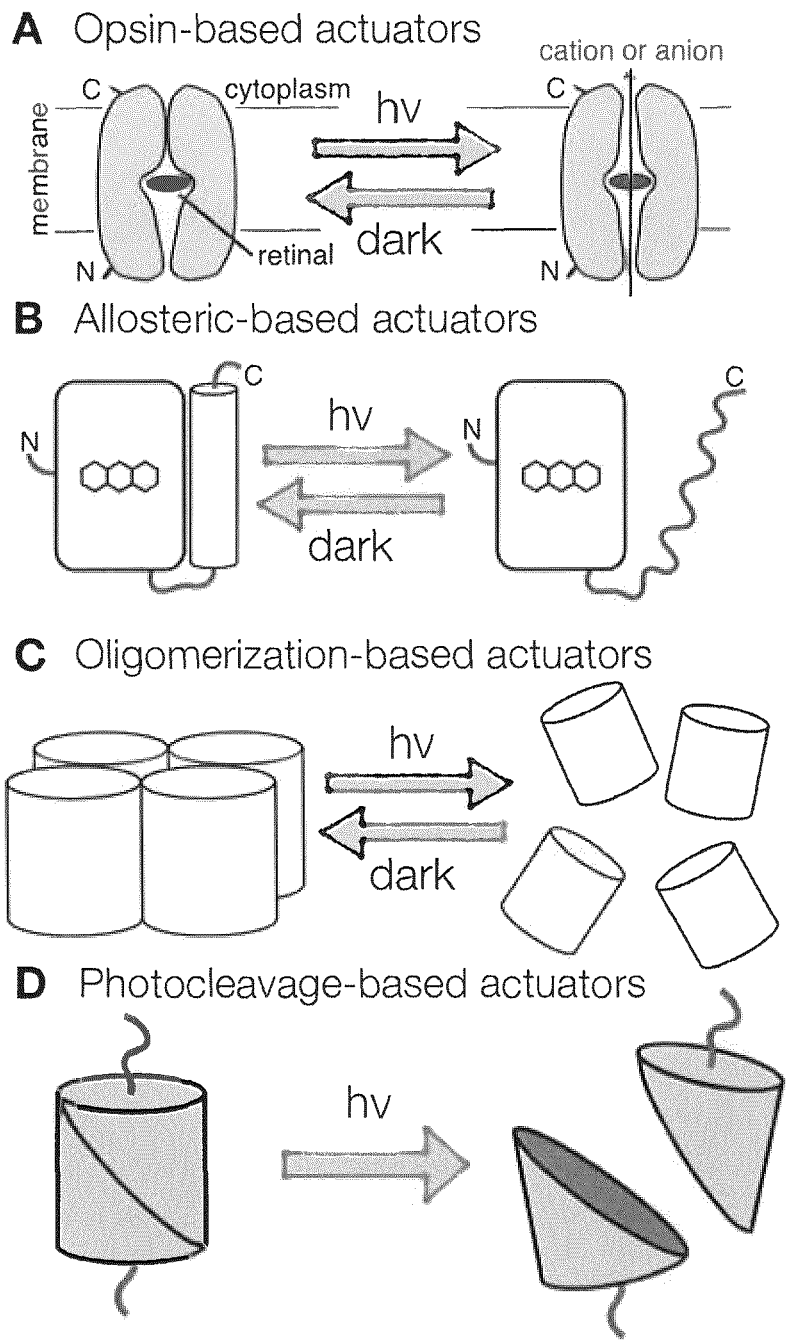
FIGS. 1A-D are schematic diagrams of the four classes of optogenetic actuators, namely opsin-based actuators (FIG. 1A); allosteric-based actuators (FIG. 1B); oligomerization-based actuators (FIG. 1C); and photocleavage-based actuators (FIG. 1D).

The present invention relates to photocleavable proteins. When describing the present invention, all terms not defined herein have their common art-recognized meanings. Such ordinary meanings may be obtained by reference to technical dictionaries, such as *Hawley's Condensed Chemical Dictionary* 14$^{th}$ Edition, by R. J. Lewis, John Wiley & Sons, New York, N.Y., 2001.

To the extent that the following description is of a specific embodiment or a particular use of the invention, it is intended to be illustrative only, and not limiting of the claimed invention. The following description is intended to cover all alternatives, modifications and equivalents that are included in the spirit and scope of the invention, as defined in the appended claims. References in the specification to "one embodiment", "an embodiment", etc., indicate that the embodiment described may include a particular aspect, feature, structure, or characteristic, but not every embodiment necessarily includes that aspect, feature, structure, or characteristic. Moreover, such phrases may, but do not necessarily, refer to the same embodiment referred to in other portions of the specification. Further, when a particular aspect, feature, structure, or characteristic is described in connection with an embodiment, it is within the knowledge of one skilled in the art to affect or connect such aspect, feature, structure, or characteristic with other embodiments, whether or not explicitly described.

The present invention comprises novel proteins which are derived from fluorescent proteins, and upon illumination, photocleave and spontaneously dissociate into at least two fragments, or release one end of an internal loop. The inventors have adopted the name PhoCle (photocleavable) proteins with a succeeding numerical identifier to identify certain variants of the present invention, and the name "circularly permuted" (cpPhoCle) to identify particular variants which contain a loop insertion.

As used herein, "photocleave" means the breaking of a covalent bond within the amino acid sequence of the protein, upon illumination of the protein with light having a suitable wavelength and energy, thereby creating a new C-terminus and a new N-terminus.

As used herein, a "loop insertion" is an internal loop, which is a secondary structural feature of the protein. An internal loop is formed by an internal sequence of amino acids. Upon photocleavage at or near one end of internal loop, the loop is released and dissociates from the protein, while still being anchored to the protein by the unreleased end.

As used herein, the term "circularly permuted" or "circular permutation" refers to a nucleic acid or protein sequence in which the circularly permuted sequence differs from the original non-circularly permuted sequence in a specific way. For a protein, the circularly permuted sequence differs in that the C-terminus in the original non-circularly permuted sequence is attached to the N-terminus in the original non-circularly permuted sequence, either directly or by way of a linking sequence of amino acids, and new C- and N-termini are created elsewhere in the sequence. A circularly permuted sequence can be conceptualized as joining the ends of an original, linear non-circularly permuted sequence to form a cyclized sequence, either at the gene level or at the protein level, and converting the cyclized sequence back to a linear sequence by breaking the bonds at a new location. Although a circularly permuted sequence can be created in this manner, as used herein, the term "circularly permuted sequence" can also include the same sequence created by other means not involving a cyclized intermediate. At the gene level, the original gene may be split at the position encoding new C- and N-termini and the original two ends joined by DNA recombinant technology.

"Randomly circularly permuted" as used herein refers to a sequence in which a circularly permuted sequence is created in which the site of circular permutation is determined by a random, semi-random or stochastic process.

In one aspect, the invention comprises methods of producing photocleavable protein. In one embodiment, exemplary proteins of the present invention may be engineered by initially generating libraries of circularly permuted variants of a green-to-red photoconvertible fluorescent protein, such as mMaple, followed by screening, directed evolution, and/or circular permuting to identify or obtain additional variants. The fluorescent protein mMaple has a characteristic His-Tyr-Gly-derived chromophore common to all green-to-red photoconvertible fluorescent proteins. In a method of preparing the photocleavable proteins of the present invention, mMaple may be circularly permuted such that a sequence break comprising new C- and N-termini is produced close to the chromophore.

Upon illumination, green-to-red photocleavage produces a peptide comprising the amino acid sequence between the sequence break and the photocleavage site. This peptide has few stabilizing interactions with the remainder of the protein and therefore spontaneously dissociates from the remainder of the protein. Since the proteins are variants of mMaple, they exhibit desirable properties of fluorescent proteins. Such properties include, but are not limited to, negligible cytotoxicity, robust expression in a wide variety of tissue and organism types, compatibility with transgenic animals, and no requirement for an exogenous cofactor.

In an alternative embodiment, the sequence break may not comprise new termini, but rather comprise a loop insertion into the amino acid sequence, which remains continuous. In this case, photocleavage results in the release of one end of the loop insertion.

In specific embodiments, the invention relates to proteins which comprise or consist of the PhoCle0.1, PhoCle0.2, PhoCle0.3, PhoCle0.4, PhoCle0.5, PhoCle0.6, PhoCle0.7, and cpPhoCle proteins; and nucleic acid constructs, vectors and host cells incorporating nucleic acid sequences which encode for the proteins of the present invention; and methods of producing and using the same.

Further, in other aspects, the invention relates to methods of using the proteins of the invention for protein localization control by release of tethered localization tags; enzyme activation by release of tethered inhibitory domains; enzyme activation by release of tethered termini; bioactive peptide/protein uncaging by release of tethered termini; surface patterning; and light-induced elution during affinity purification. Elements of the invention may be further used in the production of viruses and transgenic animals.

In one embodiment, the protein undergoes photocleavage upon illumination and spontaneously dissociates into at least two fragments. The light-induced cleavage of a covalent bond within the protein leads to spontaneous dissociation of the resulting fragments. In one embodiment, the light-induced change may be irreversible. Such proteins may be used in the engineering of a wide variety of light-regulated proteins, such as enzymes.

In one embodiment, the invention comprises a nucleic acid comprising any one of the nucleotide sequences of SEQ ID NO: 1, 3, 5, 7, 9, 11, or 13, and wherein the encoded polypeptide is photocleavable and dissociates into at least two fragments upon photocleavage. In one embodiment, the invention comprises a PhoCle nucleic acid comprising a nucleic acid sequence which encodes an amino acid sequence of one of PhoCle0.1 (SEQ ID NO: 2), PhoCle0.2 (SEQ ID NO: 4), PhoCle0.3 (SEQ ID NO: 6), PhoCle0.3 (SEQ ID NO: 8), PhoCle0.5 (SEQ ID NO: 10), PhoCle0.6 (SEQ ID NO: 12), or PhoCle0.7 (SEQ ID NO: 14).

In one embodiment, the protein undergoes photocleavage upon illumination and releases one end of an internal loop instead of dissociating into fragments. The light-induced change may be irreversible. Accordingly, the photocleavable protein can be used to uncage peptides or proteins. As used herein, the term "caging" refers to the modification of a molecule in a manner that its function is blocked by a group that can be later removed. In one embodiment, the protein comprises cpPhoCle. To prepare cpPhoCle, PhoCle0.3 is circularly permuted. cpPhoCle thus exhibits similar changes in absorbance spectrum to those observed for PhoCle.

In one embodiment, the invention comprises a cpPhoCle nucleic acid comprising a nucleic acid sequence (SEQ ID NO: 15) which encodes the amino acid sequence of cpPhoCle (SEQ ID NO: 16), or the nucleic acid or amino acid sequences at either end of the loop insertion (position 1 to position 246 and position 247 to 714 in SEQ ID NO: 15 and position 1 to position 82 and position 83 to position 237 in SEQ ID NO: 16).

Those skilled in the art will recognize that the degeneracy of the genetic code allows for a plurality of polynucleotides to encode for identical polypeptides. Accordingly, the invention includes polynucleotides of SEQ ID NOS: 1, 3, 5, 7, 9, 11, 13, and 15, and variants of polynucleotides encoding the polypeptides of SEQ ID NOS: 2, 4, 6, 8, 10, 12, 14, and 16, and variants thereof. In one embodiment, polynucleotides having at least 95%, at least 96%, at least 97%, at least 98%, or at least 99% sequence identity to the nucleotide sequences depicted in SEQ ID NOS: 1, 3, 5, 7, 9, 11, 13, and 15 are included in the invention. Methods for isolation of such polynucleotides are well known in the art (see for example, Ausubel et al., 2000).

The polynucleotides of the invention may be used to express the desired proteins in recombinantly engineered cells. In one embodiment, the invention provides polynucleotide constructs, vectors and cells comprising PhoCle0.1, PhoCle0.2, PhoCle0.3, PhoCle0.4, PhoCle0.5, PhoCle0.6, PhoCle0.7 and cpPhoCle polynucleotides. Those skilled in the art are knowledgeable in the numerous systems available for expression of a polynucleotide. All systems employ a similar approach, whereby an expression construct is assembled to include the protein coding sequence of interest and control sequences such as promoters, enhancers, and terminators, with signal sequences and selectable markers included if desired. Briefly, the expression of isolated polynucleotides encoding polypeptides is typically achieved by operably linking, for example, the DNA or cDNA to a constitutive or inducible promoter, followed by incorporation into an expression vector. The vectors can be suitable for replication and integration in either prokaryotes or eukaryotes. Typical expression vectors include transcription and translation terminators, initiation sequences, and promoters useful for regulation of the expression of the DNA. High level expression of a cloned gene is obtained by constructing expression vectors which contain a strong promoter to direct transcription, a ribosome binding site for translational initiation, and a transcription/translation terminator. Vectors may further comprise transit and targeting sequences, selectable markers, enhancers or operators. Typical vectors and means for preparing vectors are well known in the art.

In one embodiment, the invention comprises a polypeptide comprising or consisting of an amino acid sequence selected from SEQ ID NO: 2, 4, 6, 8, 10, 12, 14, or 16, or a substantially similar amino acid sequence wherein the polypeptide is photocleavable and spontaneously dissociates into at least two fragments, or releases an end of an internal loop, upon photocleavage. The polypeptides described herein can be modified and varied so long as the desired function is maintained. In one embodiment, the invention provides a polypeptide comprising an amino acid sequence having at least 95%, at least 96%, at least 97%, at least 98%, or at least 99% sequence identity to one of SEQ ID NO: 2, 4, 6, 8, 10, 12, 14, or 16, and wherein the encoded polypeptide is photocleavable and dissociates into at least two fragments, or releases an end of an internal loop. For example, the variant having substantial sequence identity may have no more than a 10% decrease or increase in function, and preferably no more than a 5% decrease or increase in function.

Those skilled in the art will appreciate that modifications (i.e., amino acid substitutions, additions, deletions and post-translational modifications) can be made to a polypeptide of the invention without eliminating or diminishing its biological activity. Some modifications may be made to facilitate the cloning, expression or purification. Guidance in determining which amino acid residues can be substituted, inserted, or deleted without abolishing biological or immunological activity can be found using computer programs well known in the art, such as DNASTAR™ software. Preferably, amino acid changes in the protein variants disclosed herein are conservative amino acid changes, i.e., substitutions of similarly charged or uncharged amino acids. Conservative amino acid substitutions (i.e., substitution of one amino acid for another amino acid of similar size, charge, polarity and conformation) or substitution of one amino acid for another within the same group (i.e., nonpolar group, polar group, positively charged group, negatively charged group) are unlikely to alter protein function adversely. Naturally occurring amino acids are generally divided into four families: acidic (aspartate, glutamate), basic (lysine, arginine, histidine), non-polar (alanine, valine, leucine, isoleucine, proline, phenylalanine, methionine, tryptophan), and uncharged polar (glycine, asparagine, glutainine, cystine, serine, threonine, tyrosine) amino acids. Phenylalanine, tryptophan, and tyrosine are sometimes classified jointly as aromatic amino acids.

In a polypeptide or protein, suitable conservative substitutions of amino acids are known to those of skill in this art and generally can be made without altering a biological activity of a resulting molecule. Those of skill in this art recognize that, in general, single amino acid substitutions in non-essential regions of a polypeptide do not substantially alter biological activity (see, e.g., Watson et al. Molecular Biology of the Gene, 4th Edition, 1987, The Benjamin/ Cummings Pub. Co., p. 224).

Variant PhoCle0.1, PhoCle0.2, PhoCle0.3, PhoCle0.4, PhoCle0.5, PhoCle0.6, PhoCle0.7, and cpPhoCle polypeptides may be obtained by mutagenesis of the corresponding polynucleotides depicted in SEQ ID NOS: 1, 3, 5, 7, 9, 11, 13, and 15 using techniques known in the art including, for example, oligonucleotide-directed mutagenesis, region-specific mutagenesis, linker-scanning mutagenesis, and site-directed mutagenesis by PCR (Ausubel et al., 2000).

Various methods for transformation or transfection of cells are known. The creation of effective viruses or animals is generally considered a goal of any project to develop a new optogenetic tool. It is this key advantage that distinguishes optogenetic actuators from related hybrid approaches that use a combination of genetically modified proteins and exogenous synthetic labels to achieve similar goals (Gorostiza and Isacoff, 2008; Szymański et al., 2013).

However, their application is generally limited to cultured cells in vitro (Banghart et al., 2004; Fortin et al., 2011; Kang et al., 2013). In one embodiment, the proteins of the invention are introduced into a cell using viral transduction or creation of transgenic animals that express the express the protein in a genetically defined subset of their tissues (Zhao et al., 2011; Madisen et al., 2012).

The polypeptides or proteins of the invention may be used for various applications. PhoCle0.1, PhoCle0.2, PhoCle0.3, PhoCle0.4, PhoCle0.5, PhoCle0.6, PhoCle0.7, or cpPhoCle, or variants thereof, may be used, for example without limitation, for protein localization control by release of tethered localization tags; enzyme activation by release of tethered inhibitory domains; enzyme activation by release of tethered termini; surface patterning; or light-induced elution during affinity purification, or similar biological techniques.

Exemplary embodiments of the present invention are described in the following Examples, which are set forth to aid in the understanding of the invention, and should not be construed to limit in any way the scope of the invention as defined in the claims which follow thereafter. As will be apparent to those skilled in the art, various modifications, adaptations and variations of the specific disclosure herein can be made without departing from the scope of the invention claimed herein.

EXAMPLES

Example 1—Preparation of mMaple (Progenitor to PhoCle)

Figure 2:
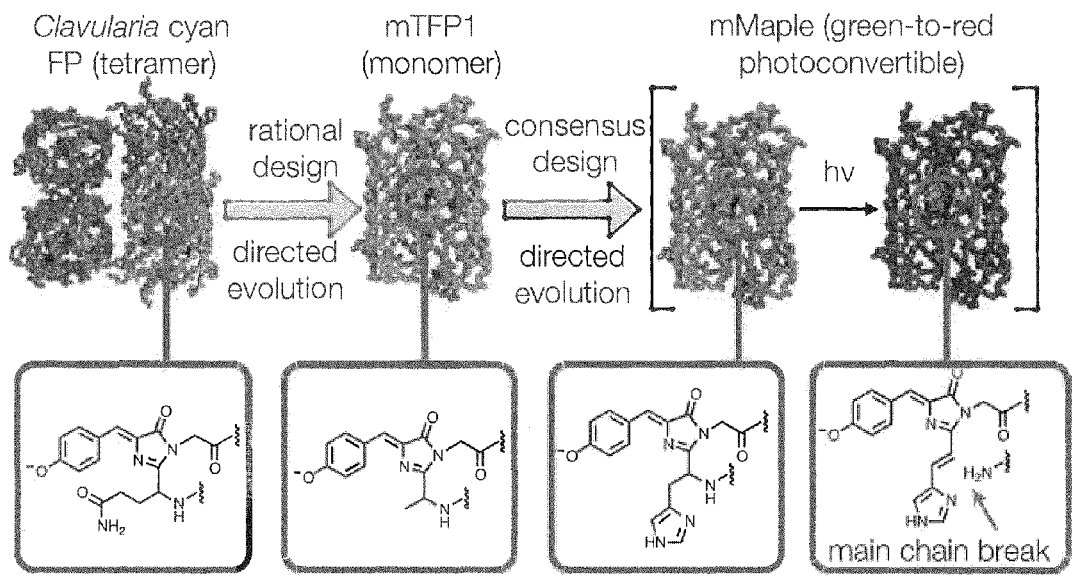
FIG. 2 is a schematic diagram showing steps for preparing mMaple.

FIG. 2 shows steps in the preparation of mMaple. Starting from a synthetic gene encoding the tetrameric cyan fluorescent protein from Clavularia coral, a monomeric variant (mTFP1) was engineered (Ai et al., 2006). While the wild-type protein has a Gln-Tyr-Gly-derived chromophore, mTFP1 has an Ala-Tyr-Gly-derived chromophore. Further engineering using consensus design and directed evolution initially yielded the green-to-red photoconvertible fluorescent protein, mClavGR2, and then mMaple (Hoi et al., 2010; McEvoy et al., 2012). Both mClavGR2 and mMaple have the characteristic His-Tyr-Gly-derived chromophore that is common to all green-to-red photoconvertible fluorescent proteins. Green-to-red photocleavage involves a photochemical reaction that extends the conjugation of the chromophore by an elimination reaction that breaks the main chain of the protein (Mizuno et al., 2003).

The photocleavage mechanism of mMaple requires that the ribosomal synthesized polypeptide first undergo protein folding and autogenic conversion of the His-Tyr-Gly (H-Y-G) sequence at the heart of the β-barrel into a green fluorescent protein-type chromophore. This chromophore exists as an equilibrium mixture of the non-fluorescent protonated (phenol) state (with absorption maximum ~400 nm) and the fluorescent anionic (phenolate) state (with absorption maximum ~480 nm). Illumination with violet light (~400 nm) leads to excitation of the protonated form. Rather than decay back to the ground state through fluorescence, the excited chromophore undergoes a β-elimination reaction which cleaves the main chain of the polypeptide at the His residue at the N-terminal side of the chromophore (Ando et al., 2002; Mizuno et al., 2003). The products of this reaction are two protein fragments. The N-terminal fragment extends from residue 1 to residue 66 and terminates in a carboxamide rather than the normal carboxylic acid. The C-terminal fragment begins with the red fluorescent chromophore (formerly residues 67-69) at its N-terminus and extends to the normal C-terminus of the protein. These two large protein fragments remain associated due to intermolecular interactions that stabilize the folded state of the protein. The chromophore remains buried in the protein and exhibits red fluorescence indefinitely.

Example 2—Engineering of PhoCle from Circularly Permuted mMaple

Libraries of circularly permuted mMaple variants with the termini either between β-sheet 3 and the central α-helix (new N- and C-termini at 54/53, 55/54, and 56/55) or between the central α-helix and β-sheet 4 (new N- and C-termini at 77/76, 78/77, and 79/78) were generated. For both locations, subsequent cleavage produced one fragment of about 10 residues and one fragment of about 230 residues. In the case of the first location, the small fragment was the N-terminal fragment and terminated just before the chromophore at residue 66 (original numbering). In the second case, the small fragment was the C-terminal fragment and started from the chromophore and ended at about residue 76, 77, or 78. For each library, the new N-terminal position and the new C-terminal position were randomized to all 20 common amino acids (NNK codon) to create a library with 400 protein variants (1024 gene variants). Using an imaging system and photocleavage chamber (Cheng and Campbell, 2006; Hoi et al., 2010), libraries were screened to identify those colonies that exhibited green to red photocleavage followed by a rapid loss of red fluorescence in the dark. Without being bound by any theory, the formation and subsequent loss of red fluorescence was likely due to dissociation of the small protein fragment and associated quenching of the fluorophore due to exposure to bulk solvent.

Figure 3:
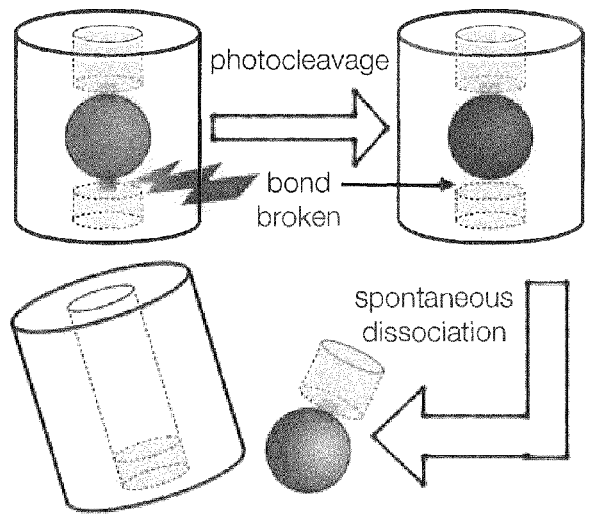
FIG. 3 is a schematic diagram showing photocleavage and spontaneous dissociation of PhoCle variants into fragments.

FIG. 3 is a schematic diagram showing the PhoCle mechanism, Violet light illumination (~400 nm) of the green form of mMaple induces an elimination reaction that cleaves the main chain of the polypeptide and forms a double bond that extends the conjugation of the chromophore to yield a red fluorophore. PhoCle variants are those variants of mMaple in which the cleavage of the main chain produces a small chromophore-containing peptide that dissociates from the larger fragment, with a concomitant loss of red fluorescence. As the chromophore of fluorescent proteins is found near the middle of the α-helix that runs through the middle of the protein, the two closest surface exposed locations for introducing new termini are immediately before, and immediately after, the central helix. Green fluorescent protein has been reported to tolerate permutation or loop insertion at these sites (Kent et al., 2009).

Figure 4:
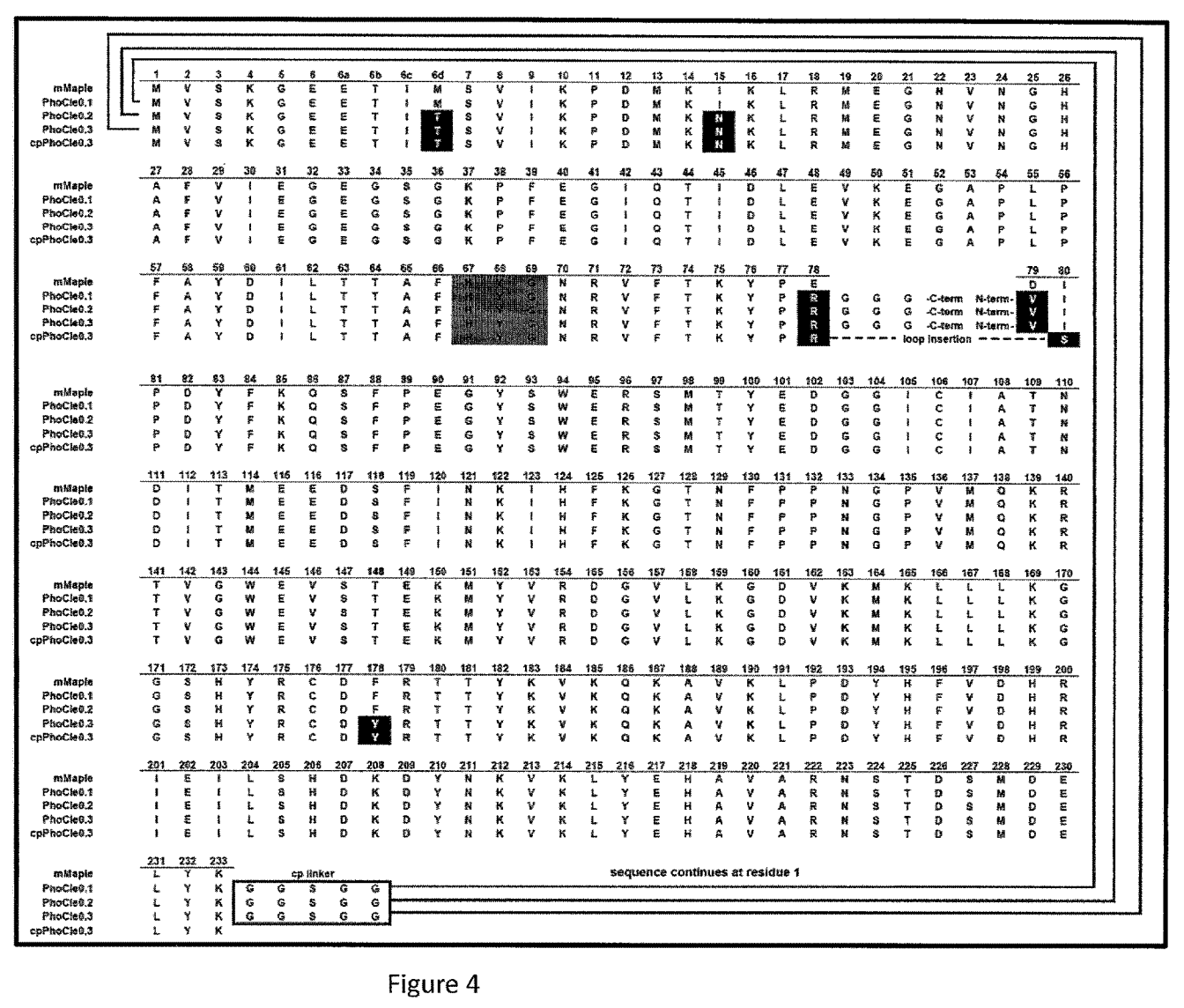

Screening of the multiple libraries led to the identification of a variant PhoCle0.1 which exhibited fluorescence changes (green to red to dark) upon photocleavage. The sequence alignment of PhoCle variants and mMaple is shown in FIG. 4. Mutations relative to mMaple are represented as white text on a black background. The chromophore-forming residues H-Y-G (67-69) are represented as black text on a gray background. The circular permutation (cp) linker sequence which links the original C-terminus and the original N-terminus is enclosed in a box. Each of PhoCle0.1, 0.2 and 0.3 are permuted at a site 12 residues distant from the chromophore, and has a Asp to Val mutation at its new N-terminus, and a Glu to Arg mutation at its new C-terminus. A short linker (three Gly residues) was also introduced at the new C-terminus. cpPhoCle is circularly permuted from PhoCle0.3. As such, it retains the same N- and C-termini as mMaple but includes a loop insertion sequence. The photocleavage reaction of cpPhoCle occurs in the same site as the other PhoCle variants, but results in release of one end of the loop rather than fragment dissociation.

Both spectroscopic and SDS-PAGE analyses of the protein before and after illumination suggested that photocleavage of PhoCle0.1 and spontaneous dissociation were occurring, with a timescale of tens of minutes ($t_{0.5}$ about 500 s). Possible improvement of these properties was pursued using further rounds of library creation and screening. Without being bound by any theory, the relatively low efficiency of photocleavage and dissociation in PhoCle0.1 may be attributed to the possibility that not all of the protein was undergoing full chromophore maturation and thus was unable to undergo photocleavage. To improve the efficiency of photocleavage, directed evolution for brighter green fluorescence and improved green to red photocleavage in bacterial colonies were performed, yielding PhoCle0.2 (equivalent to PhoCle0.1 M6dT, I15N) which exhibited improved maturation and photocleavage. To accelerate the rate of dissociation, various screening methods were tested, including the genetic fusion of a FRET pair of fluorescent proteins to either termini of PhoCle (e.g., mClover-PhoCle-mRuby2) (Lam et al., 2012). However, this approach was problematic due to complication of energy transfer from PhoCle to mRuby2. Expression of PhoCle alone and selected variants that exhibited the quickest decay of red fluorescence following photocleavage was a better approach. Peptide dissociation was the most likely reason for the loss of red fluorescence. Screening of libraries generated by error-prone PCR led to the identification of PhoCle0.3 (equivalent to PhoCle0.2 F177Y) which exhibits peptide dissociation within several minutes ($t_{0.5}$ about 120 s).

Further rounds of screening and selection led to identification of further variants PhoCle0.4 to 0.7. The mutations for each version and improved property are described below:

| Variant | Mutations | Improvements |
| --- | --- | --- |
| PhoCle0.1 | E78R, D79V | |
| PhoCle0.2 | M6dT, I15N | Improved photoconversion |
| PhoCle0.3 | F177Y | Faster dissociation |
| PhoCle0.4 | S172G | Improved thermostability |
| PhoCle0.5 | E116G, V146A | Improved thermostability |
| PhoCle0.6 | V153E | Improved thermostability and brightness |
| PhoCle0.7 | A187P | Improved thermostability and brightness |

Example 3—Characterization and Demonstrations of PhoCle Dissociation

Figure 5:
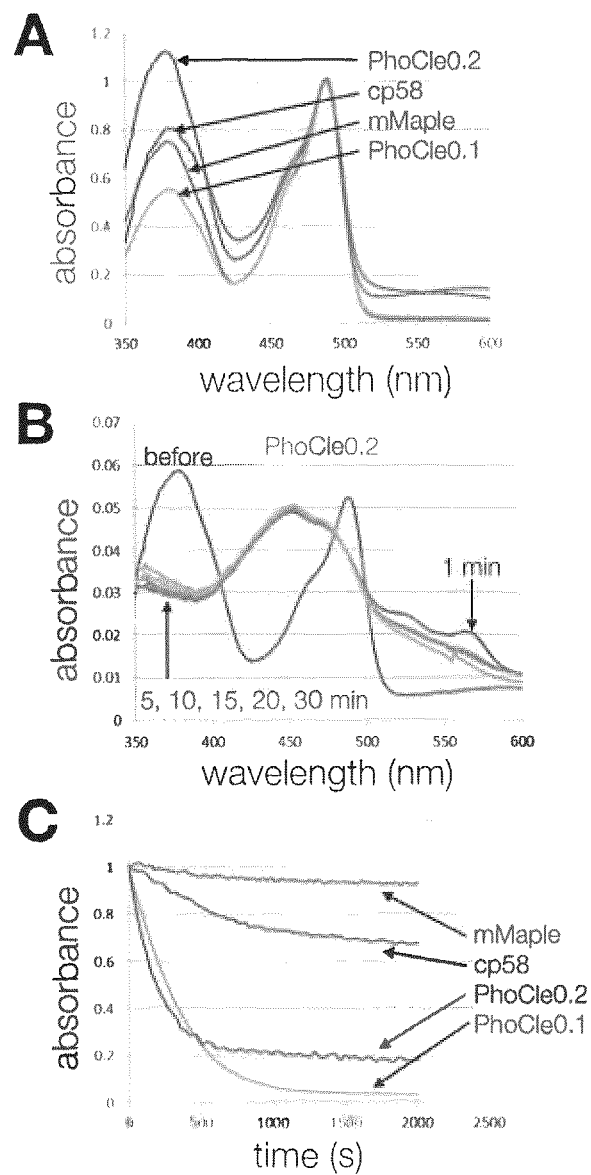
FIGS. 5A-C show spectral characterization of the PhoCle variants: purified PhoCle (FIG. 5A); the chromophore dissociated from the remainder of the protein (FIG. 5B); and the kinetics of dissociation (FIG. 5C).

UV-VIS spectroscopy indicated that PhoCle exists as a mixture of the protonated and anionic forms of the green fluorescent chromophore. Purified PhoCle has an absorbance spectrum similar to that of mMaple, since the chromophore is identical to that of the green state of mMaple prior to photocleavage (FIG. 5A). cp58 was a variant selected from libraries of circularly permuted mMaple variants with new termini between β-sheet 3 and the central α-helix (new N- and C-termini at 54/53, 55/54, and 56/55). The pronounced peak between 350 and 400 nm corresponds to the protonated state of the chromophore, while the peak between 450 and 500 nm corresponds to the anionic state of the chromophore. Excitation of the 350-400 nm species leads to photocleavage and cleavage of the main chain, while excitation of the 450-500 nm species leads to green fluorescence. Illumination of PhoCle with about 400 nm light led to a dramatic change in the absorbance spectrum (FIG. 5B). A red species that absorbs at about 540-580 nm briefly formed, but quickly converted to a third species having a broad absorbance of about 400-500 nm. The spectral properties of the third species are consistent with it being the red (photoconverted) chromophore which has dissociated from the remainder of the protein. By monitoring the loss of red absorbance following photocleavage as a function of time, the kinetics of dissociation were determined (FIG. 5C).

Figure 6:
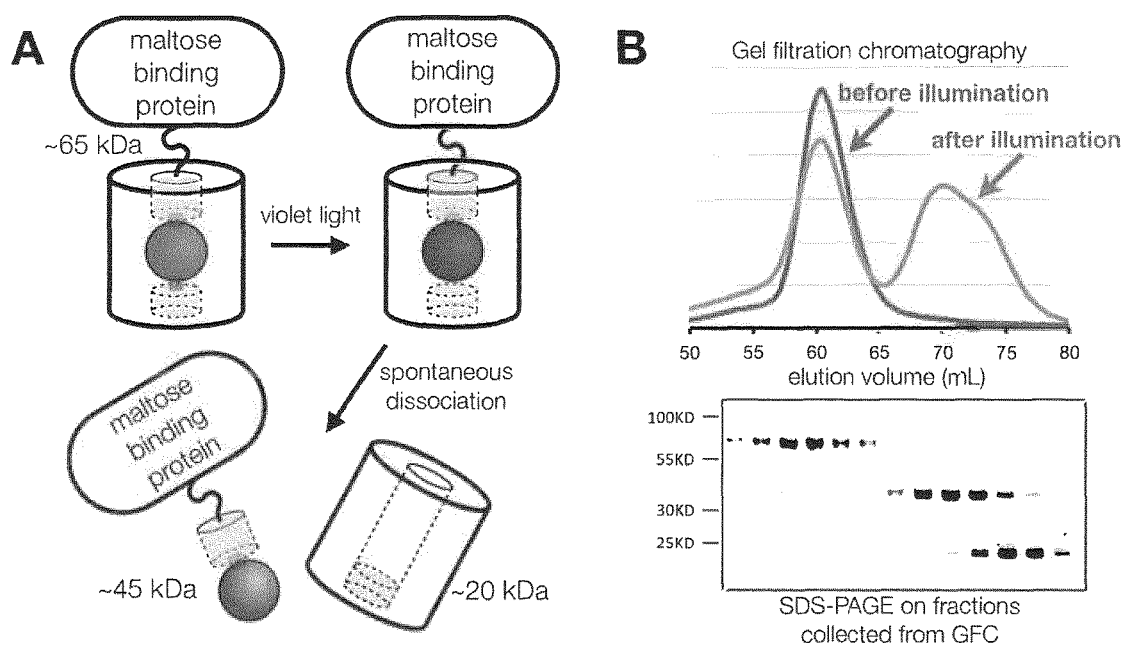
FIG. 6A is a schematic drawing showing the photocleavage reaction in vitro.
FIG. 6B shows the results of gel filtration chromatography and SDS-PAGE analysis.

FIG. 6A schematically illustrates the photocleavage reaction in vitro. The C-terminus of PhoCle0.3 was genetically fused to the N-terminus of maltose binding protein (MBP) to produce a ~65 kDa chimera. Peptide release following the photocleavage reaction yielded a ~45 kDa fragment containing MBP and the chromophore-containing peptide, and a ~20 kDa fragment composed of the remainder of the PhoCle domain. Gel filtration chromatography was used to analyze the protein before and after photocleavage (FIG. 6B). Before photocleavage, the PhoCle-MBP fusion protein eluted as a single peak at ~60 mL corresponding to the full length protein. Illumination of the purified PhoCle-MBP fusion with about 400 nm light produced a decreased peak at about 60 mL and overlapping peaks at about 70 and 74 mL. SDS-PAGE analysis of eluting fractions revealed that the ~70 mL peak is MBP fused to the chromophore-containing peptide, and the ~74 mL peak is the remainder of the PhoCle domain. These results indicate that PhoCle spontaneously dissociates following photocleavage in standard buffered solutions at room temperature.

Figure 7:
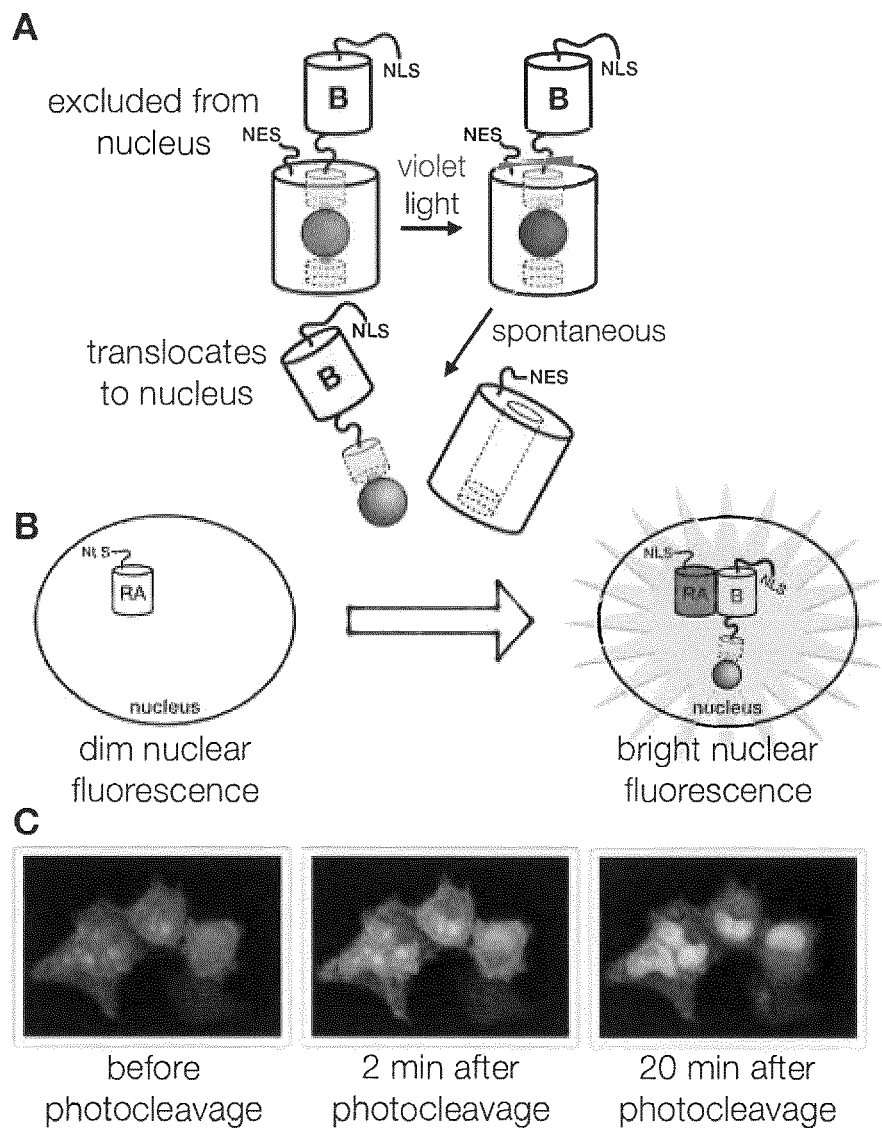
FIG. 7A is a schematic drawing showing PhoCle photocleavage in situ.
FIG. 7B is a schematic drawing showing the release, translocation, and interaction of the B copy with RA following photocleavage.
FIG. 7C are ratiometric images of cells expressing constructs.

Nuclear translocation and dimerization dependent fluorescent protein technology demonstrated that PhoCle can be used as an optogenetic tool in living cells (FIGS. 7A-C) (Alford et al., 2012; Alford et al., 2012). Two engineered proteins known as "RA" and "B" are dim in their monomeric states, but become brightly red fluorescent when allowed to interact and form a heterodimer. The B protein was fused to PhoCle0.2 for release by photocleavage. A nuclear localization sequence (NLS) was added to the B-end of the protein and a nuclear exclusion sequence (NES) was added to the PhoCle-end of the protein. Since this chimera has competing localization tags, it is generally excluded from the nucleus. When this chimera was coexpressed with a nuclear localized copy of RA, photocleavage released the B copy which then translocated to the nucleus, interacted with RA, and thereby caused a substantial increase in nuclear red fluorescence. These results show that PhoCle cleavage is rapid and robust.

Figure 8:
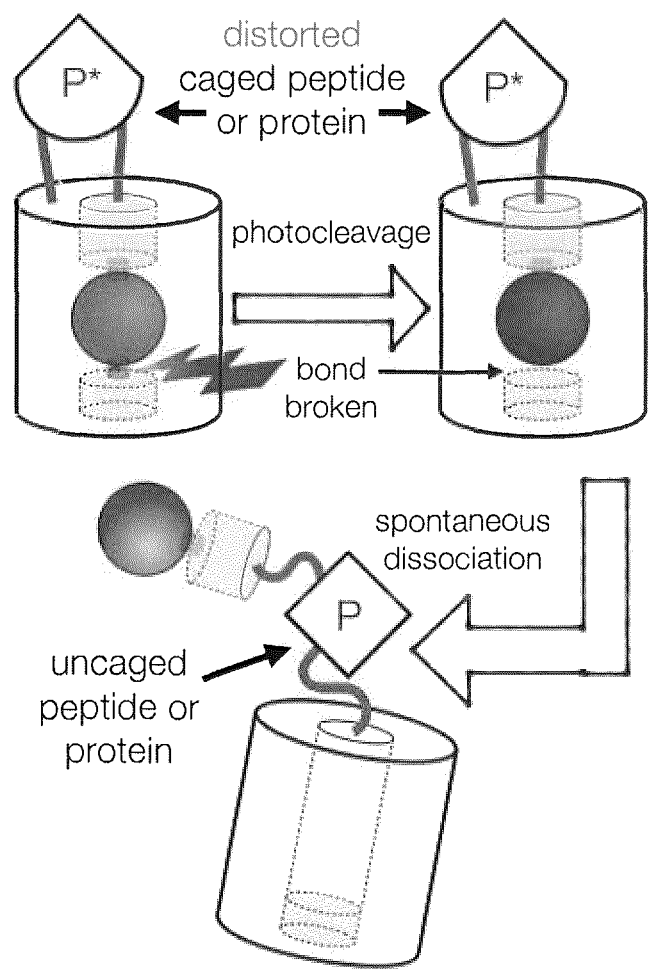
FIG. 8 is a schematic diagram showing a pathway for uncaging of a peptide/protein using cpPhoCle.

Example 4—Engineering of cpPhoCle for Optogenetic Uncaging of Peptides/Proteins A variant of PhoCle0.3 was engineered that releases one end of an internal loop upon illumination instead of completely dissociating into two fragments (FIG. 8), Circularly permuted PhoCle (cpPhoCle) exhibits similar changes in absorbance spectrum to those observed for PhoCle. While GFC analysis does not separate the protein before and after photocleavage due to the fact the molecular weight of the protein does not change (only its shape or conformation), gel-shift analysis by SDS-PAGE is consistent with the photocleavage loop release mechanism, cpPhoCle allows the uncaging of peptides/proteins with light. Genetic insertion of an active peptide/protein (P* in FIG. 8) into a loop adjacent to the central alpha-helix of cpPhoCle induces structural distortions of the peptide/protein or steric occlusion (i.e., of an enzyme active site) that renders the peptide/protein inactive. Tethering of the two ends of the peptide/protein prevents it from taking on its normal functional conformation, Upon photocleavage and release of one end of the loop from cpPhoCle, the peptide/protein (e.g., an enzyme) may assume its active conformation or bind its substrate in the case of an enzyme.

Example 5—Modulation of Protein Localization with PhoCle

A change in subcellular localization of a protein can be achieved by cleaving off localization tags or other targeting sequences linked to the protein. As shown schematically in FIG. 9A, a PhoCle fusion combines NES and NLS tags, along with a transcription factor. Upon photocleavage and dissociation, the transcription factor with an NLS tag can translocate to the nucleus.

Figure 10:
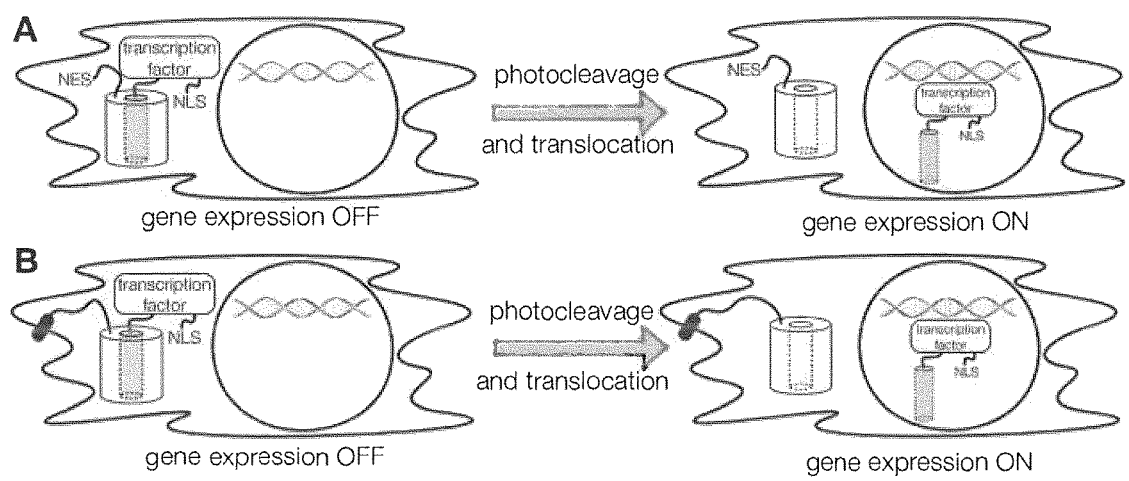
FIGS. 10A-B are schematic diagrams of pathways using PhoCle for light activated induction of gene expression.
Figure 11:
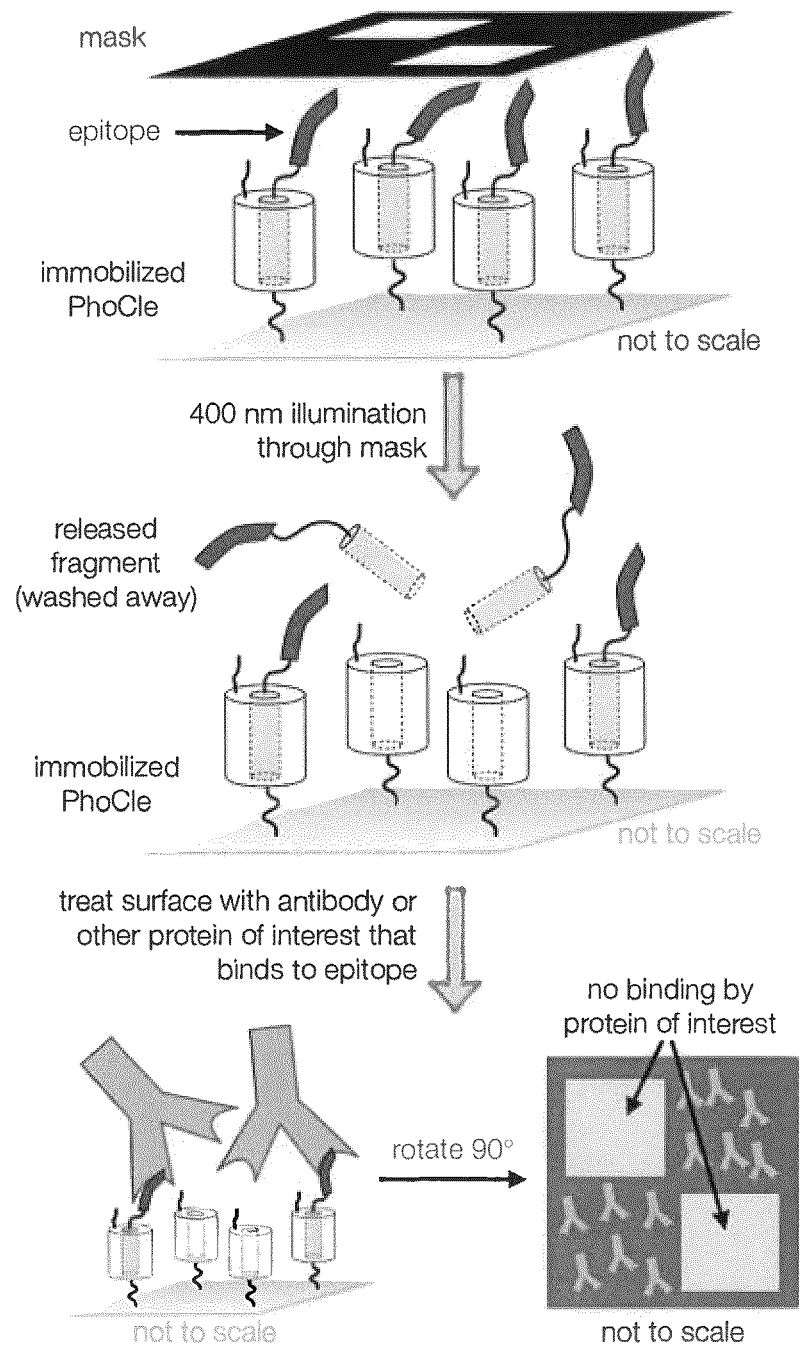
FIG. 11 is a schematic diagram of a pathway using PhoCle as a binding partner for negative surface patterning.
Figure 12:
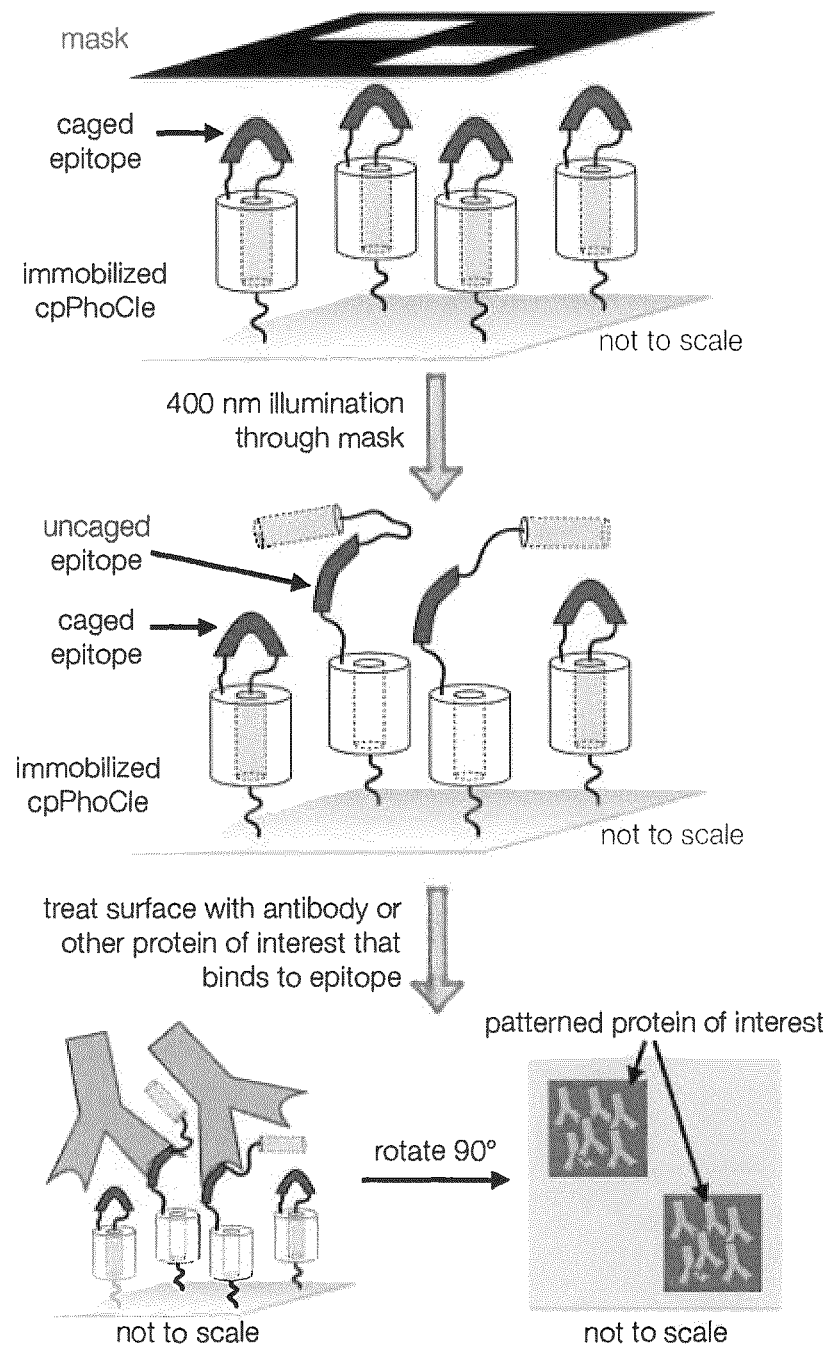
FIG. 12 is a schematic diagram of a pathway using cpPhoCle as a binding partner for positive surface patterning.
Figure 13:
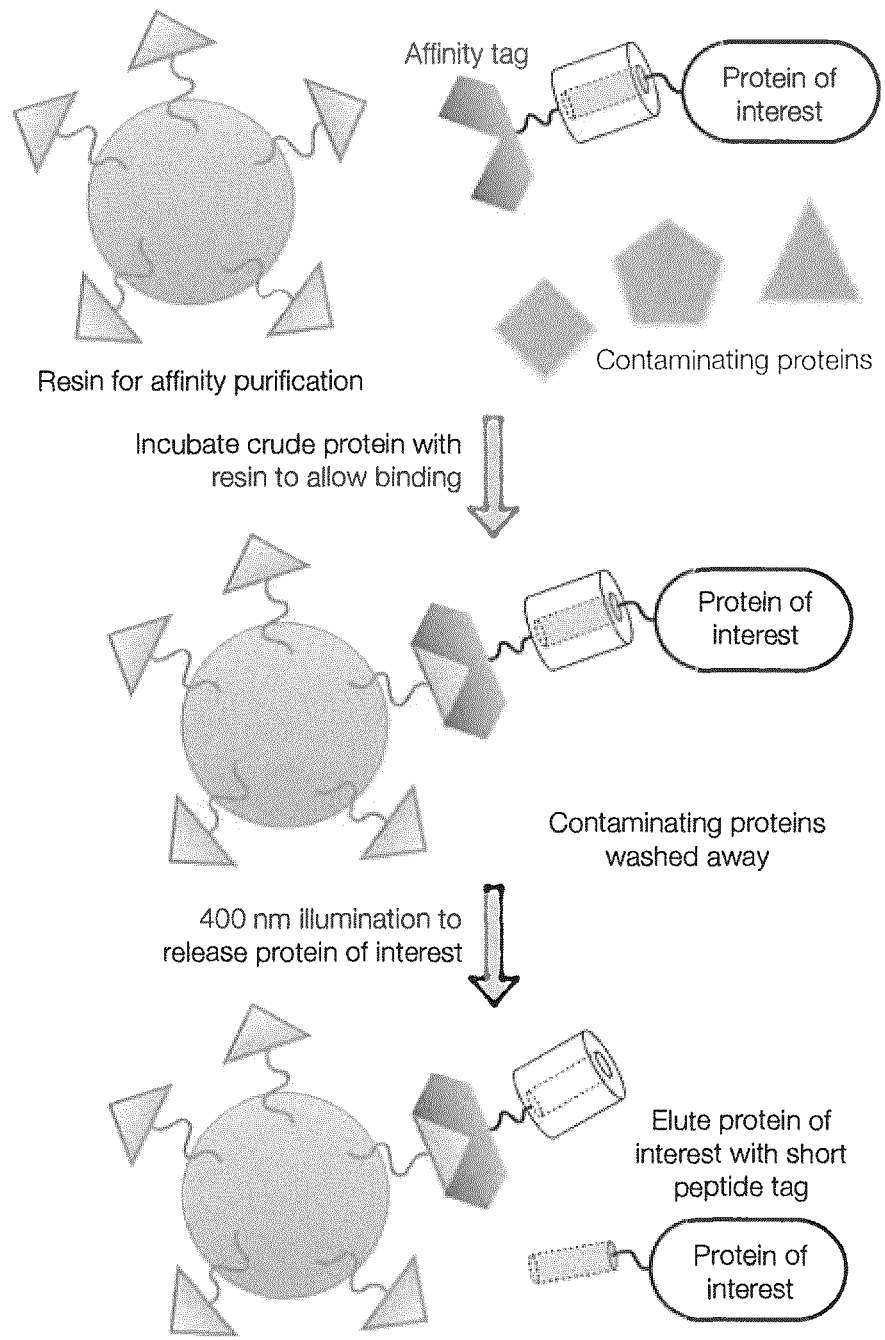
FIG. 13 is a schematic diagram showing a pathway using PhoCle as a tag in affinity purification.
Figure 22:
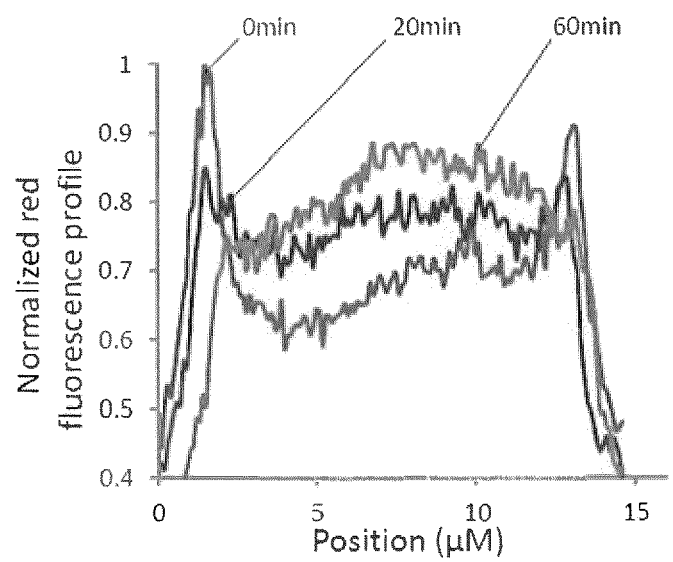
FIG. 22 is a graph showing the normalized red fluorescence profile of mCherry versus distance or position (µM) from the top arrows shown in FIGS. 21B-D.
Figure 23:
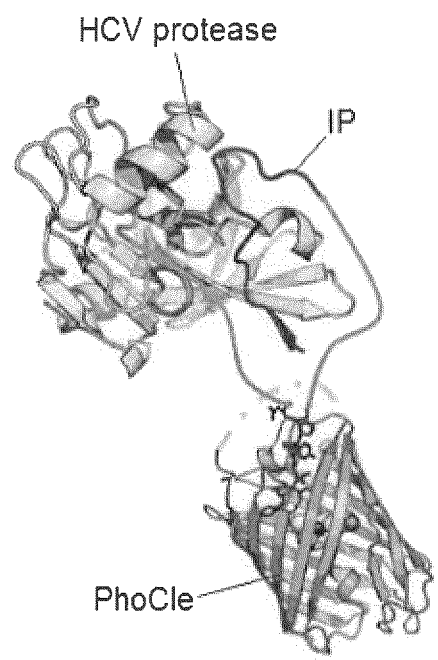
FIG. 23 is a cartoon model of the chimeric protein of IP-PhoCle-HCV protease (PhoCle model based on mTFP1, Protein Data Bank 2HQK; IP and HCV protease based on Protein Data Bank 4A1V).

PhoCle may be used for light activated induction of gene expression. Using a combination of NES and NLS tags, a transcription factor is excluded from the nucleus and thus unable to bind to its cognate promoter (FIG. 10A). Upon photocleavage, the transcription factor translocates to the nucleus and actives gene expression. Alternatively, rather than using a NES, a transcription factor-PhoCle chimera is excluded from the nucleus by tethering to a membrane, organelle, or cytoskeletal protein that is itself excluded from the nucleus (FIG. 10B). Photocleavage allows translocation to the nucleus and the activation of gene expression. Other applications may involve the release into the cytoplasm of proteins initially tethered to the plasma membrane, retained in the endoplasmic reticulum, or localized to the nucleus.

As examples, transcription factor (Gal4-vp16) and Cre recombinase were each fused to estrogen receptor ligand binding domain ($ER^{T2}$) via PhoCle linkers in order to render them photo-activatable. $ER^{T2}$ is the G521R mutant of the human estrogen receptor that is engineered to be insensitive to natural ligand (Feil et al., 1997). $ER^{T2}$ interacts with heat shock protein complexes. The PhoCle-linked fusion proteins are trapped within these complexes and inactivated by steric blocking and cytoplasmic confinement. After photocleavage, the PhoCle-linked Gal4-vp16 and Cre recombinase are released from the heat shock protein complexes and are able to enter the nucleus to be functional.

The function of PhoCle-Gal4-vp16 has been demonstrated. Mammalian cells were transfected with the gene construct pCAG $ER^{T2}$-PhoCle0.7-Gal4-vp16-PhoCle0.7-$ER^{T2}$ carrying the reporter gene pUAS-mCherry-NLS. mCherry is a widely utilized Discosoma-derived red fluorescent protein. The fluorescence images shown in FIGS. 17A-D were obtained using a 20× lens, while those shown in FIGS. 18A-D were obtained using a 40× lens, FIGS. 17A, 24C, 25A, and 25C show images of the cells 48 hours after transfection. FIGS. 17B, 24D, 25B, and 25D show images of the cells 48 hours after transfection; however, 400 nm LED (about 10 mW/cm$^2$) illumination was conducted for 180 seconds, 24 hours after transfection.

FIGS. 17A-B and 25A-B are PhoCle green channel images showing the cytoplasm of each cell exhibiting green fluorescence with (FIGS. 17B and 25B) or without illumination (FIGS. 17A and 25A). FIGS. 17C-D and 25C-D are mCherry red channel images. Illumination activated the translocation of Gal4-vp16 into the nucleus and expression of mCherry, as confirmed by exhibition of red fluoresence in the nucleus of each cell (FIGS. 17D and 25D).

The function of PhoCle-Cre has also been demonstrated. Mammalian cells were transfected with the construct $ER^{T2}$-PhoCle0.7-Cre-PhoCle0.7-$ER^{T2}$ carrying the reporter gene double floxed mCherry. The fluorescence images shown in FIGS. 19A-D were obtained using a 40× lens. FIGS. 19A and 26C show images of the cells 48 hours after transfection. FIGS. 19B and 26D show images of the cells 48 hours after transfection; however, 400 nm LED (about 10 mW/cm$^2$) illumination was conducted for 5 minutes, 24 hours after transfection.

FIGS. 19A-B are PhoCle green channel images showing the cytoplasm of each cell exhibiting green fluorescence with (FIG. 19B) or without illumination (FIG. 19A). FIGS. 19C-D are mCherry red channel images. Illumination activated the translocation of Cre recombinase into the nucleus and expression of mCherry, as confirmed by exhibition of red fluoresence in the nucleus of each cell (FIG. 19D).

Conditional activation of proteins by genetic fusion to a steroid receptor has been demonstrated to be useful for more than 70 proteins (Picard, 2015). PhoCle proteins may be combined with the well-established approach of conditional inactivation of a protein-of-interest (POI) by genetic fusion to a steroid receptor (SR). Specifically, the POI may be fused to the SR via a PhoCle linker such that the POI is in an inactive (photo-caged) state until it is photocleaved away from SR by illumination. The mechanism of inactivation involves interaction of the SR with the ubiquitous and abundant heat shock protein 90 (hsp90), leading to steric blocking, partial unfolding, or cytoplasmic confinement (for transcription factors and enzymes active in the nucleus) of the POI.

Figure 9:
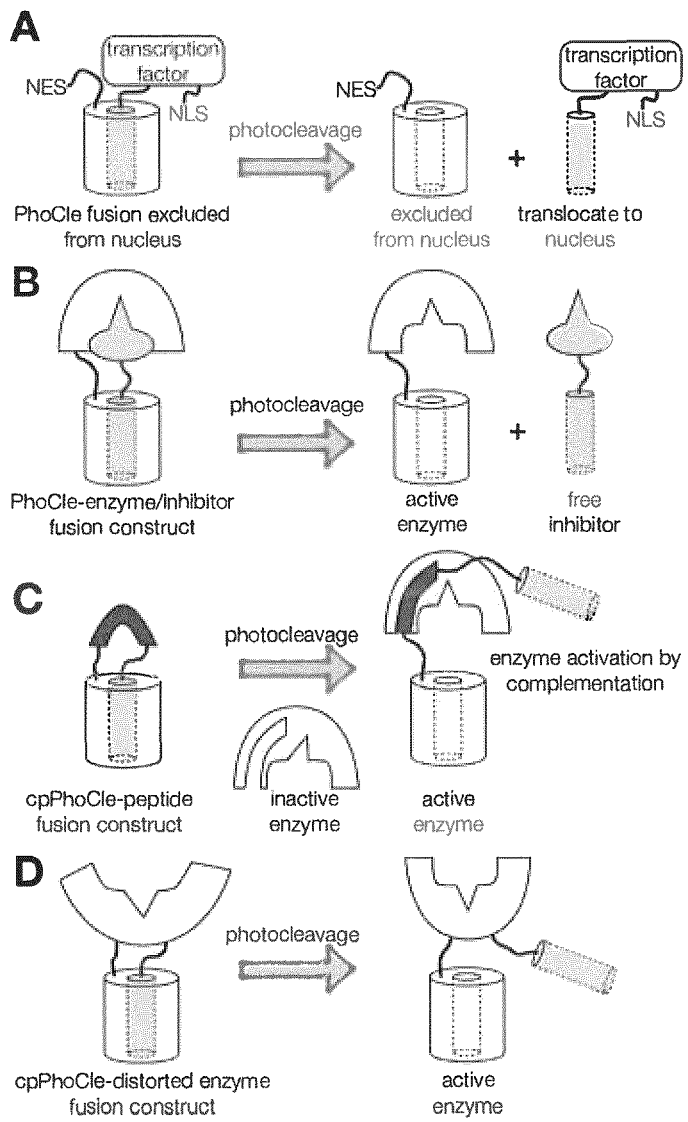
FIGS. 9A-D are schematic diagrams of applications using PhoCle and cpPhoCle.

Example 6—Protein Activation by PhoCle-Mediated Release of a Tethered Inhibitory Domain PhoCle could be used as photocleavable linker to join a protein, such as an enzyme, to a peptide/protein inhibitor (FIG. 9B). Due to the high effective concentration of the attached inhibitor, protein function is strongly inhibited. Upon dissociation of PhoCle, the inhibitor is no longer covalently linked to the protein and diffuses away, presuming that the concentration is well below the $K_d$ for the interaction. This application may be tested using the ribonuclease-inhibitor pairs barnase-barstar (Hartley, 1989); MazE-MazF (Christensen-Dalsgaard et al., 2008); the antibiotic resistance enzyme TEM-1 β-lactamase paired with the proteinaceous inhibitor BLIP (Strynadka et al., 1996); and hepatitis C NS3/4A protease paired with a peptide inhibitor (Kügler et al., 2012). This application may be useful with various protein enzymes including kinases which could be tethered to natural or artificial inhibitory sequences via PhoCle in order to produce light activatable enzymes.

Transcriptional control is one of the most appropriate, common applications of existing light-activated heterodimerizers. PhoCle may be useful in achieving similar light activated transcriptional control for example, photoactivation of the transcription factor GAL4 through the PhoCle-mediated release of the inhibitory protein partner GAL80 (Jiang et al., 2009). The $K_d$ between GAL4 and GAL80 could be adjusted into the requisite low μM range through the introduction of previously reported or crystal-structure inspired site-directed mutations that decrease the affinity of the complex.

As an example, HCV (hepatitis C virus) NS3-4A serine protease was activated by PhoCle-mediated release of a tethered inhibitory peptide in mammalian cells. A 21 peptide cofactor (4A) was first fused to the N-terminus of the HCV protease NS3 domain to make the protease more active in the cells. An inhibitory peptide (IP) was tethered to HCV protease through PhoCle0.7 ("IP-PhoCle-HCV protease").

After illumination by light at a 405 nm wavelength, the inhibitory peptide was released from the HCV protease active domain. A HCV protease substrate was inserted between the membrane tethered red fluorescent protein mCherry and membrane localization domain CAAX ("mCherry-substrate-CAAX").

FIGS. 20A-B show PhoCle green channel fluorescence images of the cytoplasm of a cell before (FIG. 20A) and after illumination (FIG. 20B). FIGS. 21A-D show mCherry red channel images before illumination (FIG. 21A) and 0 min, 20 mins, and 60 mins after illumination (FIGS. 21B-D, 29, and 30). Before illumination, red fluorescence is pronounced in the membrane. When HCV protease was activated by illumination, mCherry was released from the membrane and the red fluorescence signal moved from the membrane to the cytoplasm (arrows).

As an additional example, a photo-activatable pannexin system may be formed by combining photo-activatable HCV protease ("PA-HCV protease") and human pannexin 1 variant that is engineered to response to HCV protease.

Pannexins can form large transmembrane channels allowing the passage of ions and small molecules between intracellular and extracellular space. Although recent studies have shown a linkage between pannexin and propagation of calcium waves, regulation of vascular tone, mucociliary lung clearance, taste-bud function and neurological disorders, the precise functions of pannexins remain unclear.

FIGS. 24A-C show mammalian cells. In FIG. 24B, the cells were co-transfected with pannexin (engineered to be responsive to HCV protease) and HCV protease (active and EBFP-tagged). EBFP is a blue fluorescent variant of the green fluorescent protein variant EGFP. In FIG. 24C, cells were co-transfected with pannexin-mCherry (engineered to be responsive to HCV protease and tagged with mCherry) and HCV protease (active and EBFP-tagged). FIGS. 24B-C show that both pannexin and pannexin-mCherry were activated by HCV protease and caused cell morphology changes. In FIGS. 24B-C, the fluorescent signal was from EBFP.

Mammalian cells were co-transfected with pannexin and PA-HCV protease, and pannexin-mCherry and PA-HCV protease. FIG. 25 shows the cells before and 90 mins after illumination. The fluorescent signal represented the green fluorescence of PhoCle (IP-PhoCle-HCV protease) and was present in the cytoplasm. In the right panel (90 mins after illumination), cells with pannexin and PA-HCV protease looked similar to cells shown in FIG. 24B. Cells with pannexin-mCherry and PA-HCV protease appeared similar to cells shown in FIG. 24C. These results demonstrate that after illumination, pannexin was activated in response to the photo-activation of HCV protease.

The above results indicate that PA-HCV protease can temporally activate pannexin and cause cell morphology changes. The figures in the left panel of FIG. 25 show normal HEK 293 cells (Human Embryonic Kidney 293 cells). The figures in the right panel of FIG. 25 show pannexin photo-activation through PA-HCV protease. FIGS. 24B-C are positive controls with active pannexin (active HCV protease), HEK 293 cells are epithelial-like cells, which are polygonal in shape with regular dimensions (left panel of FIG. 25). In the top right panel of FIG. 25 (cells with pannexin and PA-HCV protease) and FIG. 24B, the cells are round and show blebs (indicated by arrows), which is indicative of a necrotic phenotype caused by activation of pannexin in the cells. In the bottom right panel of FIG. 25 (cells with pannexin-mCherry and PA-HCV protease) and FIG. 24C, the cells were responsive to pannexin activation in a different way. Without being bound by any theory, this might have been caused by tagging with mCherry. However, the bottom right panel of FIG. 25 is similar to its positive control shown in FIG. 24C.

Example 7—Peptide Uncaging by Release of Tethered Termini with cpPhoCle

A peptide inserted into the releasable loop of cpPhoCle may be constrained to a conformation that does not enable it to have its normal biological function or a diminished function (FIG. 9C). Photocleavage releases one end of the peptide which then has the conformational freedom to interact with a receptor, inhibit an enzyme, complement an enzyme, or perform any other function. Further applications may include the release of inhibitory peptides (e.g., toxins) to temporarily inhibit enzymes in the cytoplasm of cells and channels or receptors in the membrane of cells, Peptide toxins tethered to the cell surface can silence neurotransmission by effectively inhibiting calcium ion channel currents and dopamine release (Auer et al., 2010; Ibañez-Tallon and Nitabach, 2012). By caging these same peptide toxins in cpPhoCle at targeting the protein to the surface of neuronal cells using standard techniques, photoactivatable induction of inhibition may be achieved.

Example 8—Protein Uncaging by Release of Tethered Termini with cpPhoCle

Insertion of a whole protein/enzyme into the loop region of cpPhoCle distorts the structure of protein/enzyme, rendering it inactive (FIG. 9D), Upon release by photocleavage, the protein/enzyme is able to adopt its active conformation. This application may be amenable to proteins that exhibit substantial conformational dynamics, such they are only inactivated but not unfolded by this structural distortion, Examples of target proteins include, but are not limited to, Cre recombinase for optogenetic control of permanent gene activation, hepatitis C NS3/4A protease, TEV protease, or optogenetic control of protease activity.

A light-activated phospholipase C for generation of phosphotidylinositol may be a useful tool which may be created using the cpPhoCle activation strategy. Rat phosphoinositide-specific phospholipase C-$\delta 1$ isozyme can be produced in soluble form in *E. coli* (Heinz et al., 1998). In parallel, caging of the structurally homologous *Bacillus cereus* enzyme that has previously been subjected to engineering by random mutagenesis and screening for improved activity towards phosphatidylcholine, phosphatidyethanolamine, and phosphatidylserine may be conducted (Antikainen et al., 2003). These enzymes have their N- and C-termini close together in space (~7 Å, Cα-Cα; PDB ID 1PTG) which renders the enzyme highly suitable for caging using cpPhoCle. Libraries of potentially caged variants (i.e., with randomized linker compositions and lengths) may be subjected to systematic screening for light-induced activation by assaying of crude bacterial lysate for phospholipase activity using the EnzChek® Direct Phospholipase C Assay kit (Invitrogen) or fluorogenic substrates with the appropriate phosphorylation pattern (Huang et al., 2011). An aliquot of the bacterial lysate is added to two adjacent wells in a 96-well microplate format, each containing the other assay components. A mask that covers every second well is placed over the plate, and the plate is then placed under an appropriate illumination source for 60 min at room temperature. The fluorescence intensity of all wells on the plate are read and clones with the greatest difference in fluorescence between the covered and exposed wells are kept for further characterization and DNA sequencing.

Example 9—Surface Patterning with PhoCle and cpPhoCle

PhoCle and cpPhoCle may be used as binding partners to create biocompatible surfaces with proteins of interest immobilized in a designed pattern using either a negative or positive mask. For negative masking, PhoCle is engineered to have a protein-binding epitope at its C-terminus, and a surface binding peptide at its N-terminus. The protein is incubated with an appropriately modified surface (e.g., a Ni-NTA-coated surface for a His6 tagged protein or a gold surface for a cysteine tagged protein) to immobilize the protein (FIG. 11). A negative mask is designed such that light passes where it is desirable to have no protein immobilized. The masked surface is illuminated with UV or 400 nm light to induce the photocleavage reaction. After washing, the protein of interest (e.g., an antibody, streptavidin, or other protein) is applied to the surface. The protein of interest binds only in those places that are blocked by the mask. This first protein applied to the surface may serve as a primary anchor for attaching other proteins. A peptide substrate for biotin ligase is fused to the C-terminus of PhoCle. Before or after photocleavage, the surface is treated with the enzyme biotin ligase to attach biotin covalently to the remaining substrates that were blocked by the mask. The surface is then treated with streptavidin or streptavidin-fused proteins to create a highly versatile surface for immobilization of other proteins.

For positive masking, cpPhoCle is engineered to have a protein-binding peptide caged in the internal loop that is connected to the central α-helix (FIG. 12). Either the N- or C-terminus is modified with a surface binding peptide (e.g., His6 tag to bind to a Ni-NTA coated surface, or thiol-containing cysteines to bind to a gold surface) at its N-terminus. The protein is immobilized on the surface to be patterned. A positive mask is designed such that light passes where it is desirable to have protein immobilized. Illumination of the surface through the mask causes patterned uncaging of the peptide. The protein of interest (e.g., an antibody, streptavidin, or other protein) is applied to the surface and binds only in those places where light passed through the mask.

Example 10—PhoCle for Light-Induced Elution During Affinity Protein Purification PhoCle may be used as a tag for light-induced elution of desired proteins from a purification resin during affinity purification (FIG. 13). In typical affinity purification, a change in the buffer conditions (e.g., addition of imidazole or a decrease in pH for elution from Ni-NTA) is used to elute the protein; however, this often causes some proteins that are non-specifically bound to the resin to elute with the desired protein. Since photocleavage and spontaneous dissociation are unique properties of PhoCle, specific elution may be achieved of only the desired protein bound to PhoCle and the appropriate affinity tag (e.g., maltose binding protein or a $His_6$ peptide). A similar application has been demonstrated with the UV-photocleavable GH-1 from *Sulfolobus solfataricus*; however, the protein had to be illuminated for hours and denatured to unfold and dissociate the resulting fragments of GH-1 (Floyd et al., 2009). In contrast, certain PhoCle variants undergo photocleavage and spontaneous dissociation within minutes. The chromophore-containing peptide remains associated with the desired protein to provide a unique visible wavelength spectral handle that can be used to determine the concentration of the desired protein, thereby facilitating downstream applications by making the protein concentration determination a trivial and consistent procedure that works identically for any desired protein. The unique chemical reactivity of the chromophore may also be useful for further chemical modifications and labeling.

Definitions and Interpretation

The singular forms "a," "an," and "the" include plural reference unless the context clearly dictates otherwise. Thus, for example, a reference to "a plant" includes a plurality of such plants. It is further noted that the claims may be drafted to exclude any optional element. As such, this statement is intended to serve as antecedent basis for the use of exclusive terminology, such as "solely," "only," and the like, in connection with the recitation of claim elements or use of a "negative" limitation.

The term "and/or" means any one of the items, any combination of the items, or all of the items with which this term is associated.

The term "about" can refer to a variation of ±5%, +10%, ±20%, or ±25% of the value specified. For example, "about 50" percent can in some embodiments carry a variation from 45 to 55 percent. For integer ranges, the term "about" can include one or two integers greater than and/or less than a recited integer at each end of the range. Unless indicated otherwise herein, the term "about" is intended to include values and ranges proximate to the recited range that are equivalent in terms of the functionality of the composition, or the embodiment.

As will be understood by the skilled artisan, all numbers, including those expressing quantities of reagents or ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. A recited range (e.g., weight percents or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc.

As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, as used in an explicit negative limitation.

The term "contacting" refers to the act of touching, making contact, or of bringing to immediate or close proximity, including at the cellular or molecular level, for example, to bring about a physiological reaction, a chemical reaction, or a physical change, in vitro, or in vivo.

An "effective amount" refers to an amount effective to bring about a recited effect.

As used herein, the term "nucleic acid" and "polynucleotide" refers to deoxyribonucleotides or ribonucleotides and polymers thereof in either single- or double-stranded form, composed of monomers (nucleotides) containing a sugar, phosphate and a base that is either a purine or pyrimidine. Unless specifically limited, the term encompasses nucleic acids containing known analogs of natural nucleotides which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucl. Acids Res., 19:508 (1991); Ohtsuka et al., J. Biol. Chem., 260: 2605 (1985); Rossolini et al., Mol. Cell. Probes, 8:91 (1994).

Deoxyribonucleic acid (DNA) in the majority of organisms is the genetic material while ribonucleic acid (RNA) is involved in the transfer of information contained within DNA into proteins. The term "nucleotide sequence" refers to a polymer of DNA or RNA that can be single- or double-stranded, optionally containing synthetic, non-natural or altered nucleotide bases capable of incorporation into DNA or RNA polymers. A "nucleic acid fragment" is a fraction or a portion of a given nucleic acid molecule.

The terms "nucleic acid", "nucleic acid molecule", "nucleic acid fragment", "nucleic acid sequence or segment", or "polynucleotide" may also be used interchangeably with gene, cDNA, DNA and RNA encoded by a gene, e.g., genomic DNA, and even synthetic DNA sequences. The term also includes sequences that include any of the known base analogs of DNA and RNA.

The term "gene" is used broadly to refer to any segment of nucleic acid associated with a biological function. Thus, genes include coding sequences and/or the regulatory sequences required for their expression. For example, gene refers to a nucleic acid fragment that expresses mRNA, functional RNA, or specific protein, including regulatory sequences. Genes also include nonexpressed DNA segments that, for example, form recognition sequences for other proteins. Genes can be obtained from a variety of sources, including cloning from a source of interest or synthesizing from known or predicted sequence information, and may include sequences designed to have desired parameters.

A "variant" of a molecule is a sequence that is substantially similar to the sequence of the native molecule. For nucleotide sequences, variants include those sequences that, because of the degeneracy of the genetic code, encode the identical amino acid sequence of the native protein. Naturally occurring allelic variants such as these can be identified with the use of well-known molecular biology techniques, as, for example, with polymerase chain reaction (PCR) and hybridization techniques. Variant nucleotide sequences also include synthetically derived nucleotide sequences, such as those generated, for example, by using site-directed mutagenesis that encode the native protein, as well as those that encode a polypeptide having amino acid substitutions. Variant polypeptides are polypeptides having substantially similar amino acid sequences and no substantial loss or gain of function, for example, polypeptides having conservative amino acid substitutions, as described above.

"Operably-linked" refers to the association of nucleic acid sequences on single nucleic acid fragment so that the function of one is affected by the other. For example, a regulatory DNA sequence is said to be "operably linked to" or "associated with" a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or antisense orientation.

REFERENCES

The following references are incorporated herein by reference (where permitted) as if reproduced in their entirety. All references are indicative of the level of skill of those skilled in the art to which this invention pertains.

Ai, H., Hazelwood, K. L., Davidson, M, W., and Campbell, R. E. (2008). Fluorescent protein FRET pairs for ratiometric imaging of dual biosensors, Nat. Methods 5, 401-403.

Ai, H., Henderson, J, N., Remington, S. J., and Campbell, R. E. (2006). Directed evolution of a monomeric, bright and photostable version of Clavularia cyan fluorescent protein: structural characterization and applications in fluorescence imaging. Biochem. J. 400, 531-540.

Ai, H., Olenych, S. G., Wong, P., Davidson, M. W., and Campbell, R. E. (2008). Hue-shifted monomeric variants of Clavularia cyan fluorescent protein: identification of the molecular determinants of color and applications in fluorescence imaging. BMC Biol. 6, 13.

Ai, H., Shaner, N. C., Cheng, Z., Tsien, R. Y., and Campbell, R. E. (2007). Exploration of new chromophore structures leads to the identification of improved blue fluorescent proteins. Biochemistry 46, 5904-5910.

Airan, R. D., Thompson, K. R., Fenno, L. E., Bernstein, H., and Deisseroth, K. (2009). Temporally precise in vivo control of intracellular signalling. Nature 458, 1025-1029.

Akerboom, J., Calderón, N. C., Tian, L., Wabnig, S., Prigge, M., Tolö, J., Gordus, A., Orger, M. B., Severi, K. E., Macklin, J. J., et al. (2013). Genetically encoded calcium indicators for multi-color neural activity imaging and combination with optogenetics. Front. Mol. Neurosci. 6, 2.

Alford, S. C., Abdelfattah, A. S., Ding, Y., and Campbell, R. E. (2012). A fluorogenic red fluorescent protein heterodimer. Chem. Biol. 19, 353-360, Alford, S. C., Ding, Y., Simmen, T., and Campbell, R. E. (2012). Dimerization-Dependent Green and Yellow Fluorescent Proteins, ACS Synth. Biol. 1, 569-575.

Alford, S. C., Wu, J., Zhao, Y., Campbell, R. E., and Knöpfel, T. (2013). Optogenetic reporters. Biol. Cell 105, 14-29.

Ando, R., Hama, H., Yamamoto-Hino, M., Mizuno, H., and Miyawaki, A. (2002). An optical marker based on the UV-induced green-to-red photocleavage of a fluorescent protein. Proc. Natl. Acad. Sci. U.S.A 99, 12651-12656.

Antikainen, N. M., Hergenrother, P. J., Harris, M. M., Corbett, W., and Martin, S. F. (2003). Altering substrate specificity of phosphatidylcholine-preferring phospholipase C of Bacillus cereus by random mutagenesis of the headgroup binding site. Biochemistry 42, 1603-1610.

Aoki, S., Matsuo, N., Hanaya, K., Yamada, Y., and Kageyama, Y. (2009). Design and synthesis of a photocleavable biotin-linker for the photoisolation of ligand-receptor complexes based on the photolysis of 8-quinolinyl sulfonates in aqueous solution. Bioorg Med Chem 17, 3405-3413.

Auer, S., Stürzebecher, A. S., Jüttner, R., Santos-Torres, J., Hanack, C., Frahm, S., Liehl, B., and Ibañez-Tallon, I. (2010). Silencing neurotransmission with membrane-tethered toxins. Nat Methods 7, 229-236.

Baird, G. S., Zacharias, D. A., and Tsien, R. Y. (1999). Circular permutation and receptor insertion within green fluorescent proteins. Proc. Natl. Acad. Sci. U.S.A 96, 11241-11246.

Banghart, M., Borges, K., Isacoff, E., Trauner, D., and Kramer, R. H. (2004). Light-activated ion channels for remote control of neuronal firing. Nat Neurosci 7, 1381-1386.

Banghart, M. R., and Sabatini, B. L. (2012). Photoactivatable neuropeptides for spatiotemporally precise delivery of opioids in neural tissue. Neuron 73, 249-259.

Belal, A. S., Sell, B. R., Hoi, H., Davidson, M. W., and Campbell, R. E. (2013). Optimization of a genetically encoded biosensor for cyclin B1-cyclin dependent kinase 1, Mol. Biosyst.

Berndt, A., Schoenenberger, P., Mattis, J., Tye, K. M., Deisseroth, K., Hegemann, P., and Oertner, T. G. (2011). High-efficiency channelrhodopsins for fast neuronal stimulation at low light levels. Proc. Natl. Acad. Sci. U.S.A. 108, 7595-7600.

Berndt, A., Yizhar, O., Gunaydin, L. A., Hegemann, P., and Deisseroth, K. (2009). Bi-stable neural state switches. Nat. Neurosci. 12, 229-234.

Boyden, E. S., Zhang, F., Bamberg, E., Nagel, G., and Deisseroth, K. (2005). Millisecond-timescale, genetically targeted optical control of neural activity. Nat. Neurosci. 8, 1263-1268.

Bugaj, L. J., Choksi, A. T., Mesuda, C. K., Kane, R. S., and Schaffer, D. V. (2013). Optogenetic protein clustering and signaling activation in mammalian cells. Nat Methods 10, 249-252.

Campbell, R. E., and Davidson, M. W. (2010). Fluorescent Reporter Proteins. In Molecular Imaging with Reporter Genes (Cambridge Univ Pr), p. 1.

Carlson, H. J., and Campbell, R. E. (2013). Mutational Analysis of a Red Fluorescent Protein-Based Calcium Ion Indicator. Sensors 13, 11507-11521.

Carlson, H. J., Cotton, D. W., and Campbell, R. E. (2010), Circularly permuted monomeric red fluorescent proteins with new termini in the beta-sheet. Protein Sci. 19, 1490-1499.

Chen, J. K., Sinha, S., Shestopalov, I., and Ouyang, X. Photocleavable linker methods and compositions. U.S. Pat. No. 7,923,562, issued Apr. 12, 2011.

Chen, D., Gibson, E. S., and Kennedy, M. J. (2013), A light-triggered protein secretion system. J Cell Biol 201, 631-640.

Chen, T. W., Wardill, T. J., Sun, Y., Pulver, S. R., Renninger, S. L., Baohan, A., Schreiter, E. R., Kerr, R. A., Orger, M. B., Jayaraman, V., et al. (2013). Ultrasensitive fluorescent proteins for imaging neuronal activity. Nature 499, 295-300.

Cheng, Z., and Campbell, R. E. (2006), Assessing the structural stability of designed beta-hairpin peptides in the cytoplasm of live cells. Chembiochem 7, 1147-1150.

Chow, B. Y., Han, X., Dobry, A. S., Qian, X., Chuong, A. S., Li, M., Henninger, M. A., Belfort, G. M., Lin, Y., Monahan, P. E., et al. (2010). High-performance genetically targetable optical neural silencing by light-driven proton pumps. Nature 463, 98-102.

Christensen-Dalsgaard, M., Overgaard, M., Skovbo Winther, K., and Gerdes, K. (2008). RNA decay by messenger RNA interferases. Methods in enzymology 447, 521-535.

Christie, J. M., Arvai, A. S., Baxter, K. J., Heilmann, M., Pratt, A. J., O'Hara, A., Kelly, S. M., Hothorn, M., Smith, B. O., Hitomi, K., et al. (2012). Plant UVR8 photoreceptor senses UV-B by tryptophan-mediated disruption of cross-dimer salt bridges. Science 335, 1492-1496.

Christie, J. M., Gawthorne, J., Young, G., Fraser, N. J., and Roe, A. J. (2012). LOV to BLUF: flavoprotein contributions to the optogenetic toolkit. Mol Plant 5, 533-544.

Crefcoeur, R. P., Yin, R., Ulm, R., and Halazonetis, T. D. (2013). Ultraviolet-B-mediated induction of protein-protein interactions in mammalian cells. Nat Commun 4, 1779.

Ding, Y., Ai, H. W., Hoi, H., and Campbell, R. E. (2011). FRET-based biosensors for multiparameter ratiometric imaging of $Ca^{2+}$ dynamics and caspase-3 activity in single cells. Anal. Chem. 83, 9687-9693.

Fan, H. Y., Morgan, S. A., Brechun, K. E., Chen, Y. Y., Jaikaran, A. S., and Woolley, G. A. (2011). Improving a designed photocontrolled DNA-binding protein. Biochemistry 50, 1226-1237.

Fehrentz, T., Schönberger, M., and Trauner, D. (2011). Optochemical Genetics. Angew. Chem. Int. Edn. Engl.

Feil, R., Wagner, J., Metzger, D., and Chambon, P. (1997) Regulation of Cre recombinase activity by mutated estrogen receptor ligand-binding domains, Biochem. Biophys. Res. Commun. 237(3):752-7.

Fenno, L., Yizhar, O., and Deisseroth, K. (2011). The development and application of optogenetics. Annu. Rev. Neurosci. 34, 389-412.

Floyd, N., Oldham, N. J., Eyles, C. J., Taylor, S., Filatov, D. A., Brouard, M., and Davis, B. G. (2009). Photoinduced, family-specific, site-selective cleavage of TIM-barrel proteins. J Am Chem Soc 131, 12518-12519, Fortin, D. L., Dunn, T. W., Fedorchak, A., Allen, D., Montpetit, R., Banghart, M. R., Trauner, D., Adelman, J. P., and Kramer, R. H. (2011). Optogenetic photochemical control of designer K+ channels in mammalian neurons. J Neurophysiol 106, 488-496.

Gorostiza, P., and Isacoff, E. Y. (2008). Optical switches for remote and noninvasive control of cell signaling. Science 322, 395-399.

Gunaydin, L. A., Yizhar, O., Berndt, A., Sohal, V. S., Deisseroth, K., and Hegemann, P. (2010). Ultrafast optogenetic control. Nat. Neurosci. 13, 387-392.

Haramura, M. and Tanaka, A. Solid support having ligand immobilized thereon by using photocleavable linker, U.S. Pat. No. 7,456,022, issued Nov. 25, 2008.

Hartley, R. W. (1989). Barnase and barstar: two small proteins to fold and fit together. Trends Biochem, Sci. 14, 450-454, Hattori, M., Haga, S., Takakura, H., Ozaki, M., and Ozawa, T. (2013). Sustained accurate recording of intracellular acidification in living tissues with a photo-controllable bioluminescent protein. Proc Natl Acad Sci USA 110, 9332-9337.

Heinz, D. W., Essen, L. O., and Williams, R. L. (1998). Structural and mechanistic comparison of prokaryotic and eukaryotic phosphoinositide-specific phospholipases C. J. Mol. Biol., 275, 635-650.

Henderson, J. N., Ai, H. W., Campbell, R. E., and Remington, S. J. (2007). Structural basis for reversible photobleaching of a green fluorescent protein homologue. Proc. Natl. Acad. Sci. U.S.A. 104, 6672-6677.

Hertel, F., and Zhang, J. (2013). Monitoring of post-translational modification dynamics with genetically encoded fluorescent reporters. Biopolymers.

Hoi, H., Howe, E. S., Ding, Y., Zhang, W., Baird, M. A., Sell, B. R., Allen, J. R., Davidson, M. W., and Campbell, R. E. (2013). An Engineered Monomeric Zoanthus sp. Yellow Fluorescent Protein, Chem Biol 20, 1296-1304.

Hoi, H., Matsuda, T., Nagai, T., and Campbell, R. E. (2013). Highlightable Ca2+ indicators for live cell imaging. J. Am, Chem. Soc. 135, 46-49.

Hoi, H., Shaner, N. C., Davidson, M. W., Cairo, C. W., Wang, J., and Campbell, R. E. (2010). A monomeric photoconvertible fluorescent protein for imaging of dynamic protein localization. J. Mol. Biol. 401, 776-791.

Huang, W., Hicks, S. N., Sondek, J., and Zhang, Q. (2011), A fluorogenic, small molecule reporter for mammalian phospholipase C isozymes. ACS Chem. Biol. 6, 223-228.

Ibañez-Tallon, I., and Nitabach, M. N. (2012). Tethering toxins and peptide ligands for modulation of neuronal function. Curr Opin Neurobiol 22, 72-78.

Ibraheem, A., and Campbell, R. E. (2010). Designs and applications of fluorescent protein-based biosensors. Curr. Opin. Chem. Biol, 14, 30-36.

Ibraheem, A., Yap, H., Ding, Y., and Campbell, R. E. (2011). A bacteria colony-based screen for optimal linker combinations in genetically encoded biosensors, BMC Biotechnol. 11, 105.

Idevall-Hagren, O., Dickson, E. J., Hille, B., Toomre, D. K., and De Camilli, P. (2012). Optogenetic control of phosphoinositide metabolism. Proc Natl Acad Sci USA 109, E2316-E2323.

Imamoto, Y., Kamikubo, H., Harigai, M., Shimizu, N., and Kataoka, M. (2002). Light-induced global conformational change of photoactive yellow protein in solution. Biochemistry 41, 13595-13601.

Iseki, M., Matsunaga, S., Murakami, A., Ohno, K., Shiga, K., Yoshida, K., Sugai, M., Takahashi, T., Hori, T., and Watanabe, M. (2002). A blue-light-activated adenylyl cyclase mediates photoavoidance in *Euglena gracilis*. Nature 415, 1047-1051.

Jiang, F., Frey, B, R., Evans, M. L., Friel, J. C., and Hopper, J. E. (2009). Gene activation by dissociation of an inhibitor from a transcriptional activation domain. Mol Cell Biol 29, 5604-5610.

Jin, L., Han, Z., Platisa, J., Wooltorton, J. R., Cohen, L. B., and Pieribone, V. A. (2012). Single action potentials and subthreshold electrical events imaged in neurons with a fluorescent protein voltage probe. Neuron 75, 779-785.

Johnson, D. E., Ai, H. W., Wong, P., Young, J. D., Campbell, R. E., and Casey, J. R. (2009). Red Fluorescent Protein pH Biosensor to Detect Concentrative Nucleoside Transport. J. Biol. Chem. 284, 20499-20511.

Kakumoto, T., and Nakata, T. (2013). Optogenetic control of PIP3:PIP3 is sufficient to induce the actin-based active part of growth cones and is regulated via endocytosis. PLoS One 8, e70861.

Kang, J.-Y., Kawaguchi, D., Coin, I., Xiang, Z., OLeary, D. D., Slesinger, P. A., and Wang, L. (2013). In Vivo Expression of a Light-Activatable Potassium Channel Using Unnatural Amino Acids. Neuron 80, 358-370.

Karunarathne, W. K., Giri, L., Patel, A. K., Venkatesh, K. V., and Gautam, N. (2013). Optical control demonstrates switch-like PIP3 dynamics underlying the initiation of immune cell migration. Proc Natl Acad Sci USA 110, E1575-E1583.

Kennedy, M. J., Hughes, R. M., Peteya, L. A., Schwartz, J. W., Ehlers, M. D., and Tucker, C. L. (2010). Rapid blue-light-mediated induction of protein interactions in living cells. Nat Methods 7, 973-975.

Kent, K. P., Oltrogge, L. M., and Boxer, S. G. (2009). Synthetic control of green fluorescent protein. J Am Chem Soc 131, 15988-15989.

Klare, J. P., Chizhov, I., and Engelhard, M. (2008). Microbial rhodopsins: scaffolds for ion pumps, channels, and sensors. Results Probl. Cell Differ. 45, 73-122.

Knopfel, T., Lin, M. Z., Levskaya, A., Tian, L., Lin, J. Y., and Boyden, E. S. (2010). Toward the second generation of optogenetic tools. J. Neurosci. 30, 14998-15004.

Kramer, R. H., Mourot, A., and Adesnik, H. (2013). Optogenetic pharmacology for control of native neuronal signaling proteins. Nat Neurosci 16, 816-823.

Knügler, J., Schmelz, S., Gentzsch, J., Haid, S., Pollmann, E., van den Heuvel, J., Franke, R., Pietschmann, T., Heinz, D. W., and Collins, J. (2012). High affinity peptide inhibitors of the hepatitis C virus NS3-4A protease refractory to common resistant mutants. J Biol Chem 287, 39224-39232.

Lam, A. J., St-Pierre, F., Gong, Y., Marshall, J. D., Cranfill, P. J., Baird, M. A., McKeown, M. R., Wiedenmann, J., Davidson, M. W., Schnitzer, M. J., et al. (2012). Improving FRET dynamic range with bright green and red fluorescent proteins. Nat. Methods 9, 1005-1012.

Levskaya, A., Weiner, O. D., Lim, W. A., and Voigt, C. A. (2009). Spatiotemporal control of cell signalling using a light-switchable protein interaction. Nature 461, 997-1001.

Li, Y., Sierra, A. M., Ai, H. W., and Campbell, R. E. (2008). Identification of sites within a monomeric red fluorescent protein that tolerate peptide insertion and testing of corresponding circular permutations. Photochem. Photobiol. 84, 111-119.

Lungu, O. I., Hallett, R. A., Choi, E. J., Aiken, M. J., Hahn, K. M., and Kuhlman, B. (2012). Designing photoswitchable peptides using the AsLOV2 domain. Chem Biol 19, 507-517.

Madisen, L., Mao, T., Koch, H., Zhuo, J. M., Berenyi, A., Fujisawa, S., Hsu, Y. W., Garcia, A. J., Gu, X., Zanella, S., et al. (2012). A toolbox of Cre-dependent optogenetic transgenic mice for light-induced activation and silencing. Nat. Neurosci. 15, 793-802.

McEvoy, A. L., Hoi, H., Bates, M., Platonova, E., Cranfill, P. J., Davidson, M. W., Ewers, H., Liphardt, J., and Campbell, R. E. (2012), mMaple: a photoconvertible fluorescent protein for use in multiple imaging modalities, PLoS ONE 7, e51314.

Mills, E., Chen, X., Pham, E., Wong, S., and Truong, K. (2011). Engineering a photoactivated caspase-7 for rapid induction of apoptosis. ACS synthetic biology 1, 75-82.

Mizuno, H., Mal, T. K., Tong, K. I., Ando, R., Furuta, T., Ikura, M., and Miyawaki, A. (2003). Photo-induced peptide cleavage in the green-to-red conversion of a fluorescent protein. Mol. Cell. 12, 1051-1058.

Mizuno, H., Mal, T. K., Wälchli, M., Kikuchi, A., Fukano, T., Ando, R., Jeyakanthan, J., Taka, J., Shiro, Y., and Ikura, M. (2008). Light-dependent regulation of structural flexibility in a photochromic fluorescent protein. Proceedings of the National Academy of Sciences 105, 9227-9232.

Morgan, S. A., and Woolley, G. A. (2010), A photoswitchable DNA-binding protein based on a truncated GCN4-photoactive yellow protein chimera. Photochem Photobiol Sci 9, 1320-1326.

Mutoh, H., Akemann, W., and Knopfel, T. (2012), Genetically engineered fluorescent voltage reporters. ACS Chem. Neurosci. 3, 585-592.

Müller, K., and Weber, W. (2013). Optogenetic tools for mammalian systems. Mol Biosyst 9, 596-608.

Müller, K., Engesser, R., Timmer, J., Nagy, F., Zurbriggen, M. D., and Weber, W. (2013). Synthesis of phycocyanobilin in mammalian cells. Chem Commun (Camb) 49, 8970-8972.

Nagai, T., Yamada, S., Tominaga, T., Ichikawa, M., and Miyawaki, A. (2004). Expanded dynamic range of fluorescent indicators for Ca2+ by circularly permuted yellow fluorescent proteins. Proc. Natl. Acad. Sci. U.S.A. 101, 10554-10559.

Nagel, G., Szellas, T., Huhn, W., Kateriya, S., Adeishvili, N., Berthold, P., Ollig, D., Hegemann, P., and Bamberg, E. (2003). Channelrhodopsin-2, a directly light-gated cation-selective membrane channel, Proc. Natl. Acad. Sci. U.S.A. 100, 13940-13945.

Olejnik, J., Sonar, S., Krzymañska-Olejnik, E., and Rothschild, K. J. (1995). Photocleavable biotin derivatives: a versatile approach for the isolation of biomolecules. Proc. Natl. Acad. Sci. U.S.A. 92, 7590-7594.

Pandori, M. W., Hobson, D. A., Olejnik, J., Krzymanska-Olejnik, E., Rothschild, K. J., Palmer, A. A., Phillips, T. J., and Sano, T. (2002). Photochemical control of the infectivity of adenoviral vectors using a novel photocleavable biotinylation reagent. Chem. Biol. 9, 567-573.

Pathak, G. P., Vrana, J. D., and Tucker, C. L. (2013). Optogenetic control of cell function using engineered photoreceptors. Biol Cell 105, 59-72.

Picard, D. (2015) Current list of HBD fusion proteins. picard.ch/downloads/fusions.pdf.

Prigge, M., Schneider, F., Tsunoda, S. P., Shilyansky, C., Wietek, J., Deisseroth, K., and Hegemann, P. (2012). Color-tuned channelrhodopsins for multiwavelength optogenetics. J. Biol. Chem. 287, 31804-31812.

Renicke, C., Schuster, D., Usherenko, S., Essen, L. O., and Taxis, C. (2013). A LOV2 domain-based optogenetic tool to control protein degradation and cellular function. Chem Biol 20, 619-626.

Rizzini, L., Favory, J. J., Cloix, C., Faggionato, D., O'Hara, A., Kaiserli, E., Baumeister, R., Schafer, E., Nagy, F., Jenkins, G. I., et al. (2011). Perception of UV-B by the *Arabidopsis* UVR8 protein, Science 332, 103-106.

Rothschild, K. J., Sonar, S. M. and Olejnik, J. Photocleavable bioreactive agents. U.S. Pat. No. 7,485,427, issued Feb. 3, 2009.

Rothschild, K. J., Sonar, S. M. and Olejnik, J. Photocleavable agents and conjugates for the detection and isolation of biomolecules. U.S. Pat. No. 6,589,736, issued Jul. 8, 2003.

Schierling, B., and Pingoud, A. (2012). Controlling the DNA Cleavage Activity of Light-Inducible Chimeric Endonucleases by Bidirectional Photoactivation. Bioconjug Chem.

Schroder-Lang, S., Schwärzel, M., Seifert, R., Strünker, T., Kateriya, S., Looser, J., Watanabe, M., Kaupp, U. B., Hegemann, P., and Nagel, G. (2007). Fast manipulation of cellular cAMP level by light in vivo. Nat. Methods 4, 39-42.

Shimizu-Sato, S., Huq, E., Tepperman, J. M., and Quail, P. H. (2002). A light-switchable gene promoter system. Nat Biotechnol 20, 1041-1044.

Stierl, M., Stumpf, P., Udwari, D., Gueta, R., Hagedorn, R., Losi, A., Gärtner, W., Petereit, L., Efetova, M., Schwarzel, M., et al. (2011). Light modulation of cellular cAMP by a small bacterial photoactivated adenylyl cyclase, bPAC, of the soil bacterium Beggiatoa. J. Biol. Chem. 286, 1181-1188.

Strickland, D., Lin, Y., Wagner, E., Hope, C. M., Zayner, J., Antoniou, C., Sosnick, T. R., Weiss, E. L., and Glotzer, M. (2012). TULIPs: tunable, light-controlled interacting protein tags for cell biology. Nat Methods 9, 379-384.

Strickland, D., Yao, X., Gawlak, G., Rosen, M. K., Gardner, K. H., and Sosnick, T. R. (2010). Rationally improving LOV domain-based photoswitches. Nat. Methods 7, 623-626.

Strynadka, N. C., Jensen, S. E., Alzari, P. M., and James, M. N. (1996). A potent new mode of beta-lactamase inhibition revealed by the 1.7 A X-ray crystallographic structure of the TEM-1-BLIP complex. Nat Struct Biol 3, 290-297.

Szymanski, W., Beierle, J. M., Kistemaker, H. A., Velema, W. A., and Feringa, B. L. (2013), Reversible Photocontrol of Biological Systems by the Incorporation of Molecular Photoswitches. Chem Rev.

Toettcher, J. E., Gong, D., Lim, W. A., and Weiner, O. D. (2011). Light-based feedback for controlling intracellular signaling dynamics. Nat Methods 8, 837-839.

Topell, S., Hennecke, J., and Glockshuber, R. (1999). Circularly permuted variants of the green fluorescent protein. FEBS Lett. 457, 283-289.

Tsien, R. Y. (1998). The green fluorescent protein. Annu. Rev. Biochem. 67, 509-544.

Ui, M., Tanaka, Y., Araki, Y., Wada, T., Takei, T., Tsumoto, K., Endo, S., and Kinbara, K. (2012). Application of photoactive yellow protein as a photoresponsive module for controlling hemolytic activity of staphylococcal α-hemolysin. Chem Commun (Camb) 48, 4737-4739.

Wirkner, M., Alonso, J. M., Maus, V., Salierno, M., Lee, T. T., Garcia, A. J., and del Campo, A. (2011). Triggered cell release from materials using bioadhesive photocleavable linkers. Adv Mater 23, 3907-3910.

Wu, D., Hu, Q., Yan, Z., Chen, W., Yan, C., Huang, X., Zhang, J., Yang, P., Deng, H., Wang, J., et al. (2012). Structural basis of ultraviolet-B perception by UVR8. Nature 484, 214-219.

Wu, J., Liu, L., Matsuda, T., Zhao, Y., Rebane, A., Drobizhev, M., Chang, Y. F., Araki, S., Arai, Y., March, K., et al. (2013). Improved orange and red $Ca^{2+}$ indicators and photophysical considerations for optogenetic applications. ACS Chem. Neurosci. 4, 963-972.

Wu, Y. I., Frey, D., Lungu, O. I., Jaehrig, A., Schlichting, I., Kuhlman, B., and Hahn, K. M. (2009). A genetically encoded photoactivatable Rac controls the motility of living cells. Nature 461, 104-108.

Yang, X., Jost, A. P., Weiner, O. D., and Tang, C. (2013). A light-inducible organelle-targeting system for dynamically activating and inactivating signaling in budding yeast. Mol Biol Cell 24, 2419-2430.

Yazawa, M., Sadaghiani, A. M., Hsueh, B., and Dolmetsch, R. E. (2009). Induction of protein-protein interactions in live cells using light. Nat Biotechnol 27, 941-945.

Yizhar, O., Fenno, L. E., Davidson, T. J., Mogri, M., and Deisseroth, K. (2011). Optogenetics in neural systems. Neuron 71, 9-34.

Zhang, F., Prigge, M., Beyrière, F., Tsunoda, S. P., Mattis, J., Yizhar, O., Hegemann, P., and Deisseroth, K. (2008). Red-shifted optogenetic excitation: a tool for fast neural control derived from Volvox carteri. Nat. Neurosci. 11, 631-633.

Zhang, F., Wang, L. P., Brauner, M., Liewald, J. F., Kay, K., Watzke, N., Wood, P. G., Bamberg, E., Nagel, G., Gottschalk, A., et al. (2007). Multimodal fast optical interrogation of neural circuitry. Nature 446, 633-639.

Zhao, S., Ting, J. T., Atallah, H. E., Qiu, L., Tan, J., Gloss, B., Augustine, G. J., Deisseroth, K., Luo, M., Graybiel, A. M., et al. (2011). Cell type-specific channelrhodopsin-2 transgenic mice for optogenetic dissection of neural circuitry function. Nat. Methods 8, 745-752.

Zhao, Y., Araki, S., Wu, J., Teramoto, T., Chang, Y. F., Nakano, M., Abdelfattah, A. S., Fujiwara, M., Ishihara, T., Nagai, T., et al. (2011). An expanded palette of genetically encoded $Ca^{2+}$ indicators. Science 333, 1888-1891.

Zhou, X. X., Chung, H. K., Lam, A. J., and Lin, M. Z. (2012). Optical control of protein activity by fluorescent protein domains. Science 338, 810-814.

What is claimed is:

1. A photocleavable protein comprising a His-Tyr-Gly chromophore, which protein comprises a circular permutation of the amino acid sequence of SEQ ID. NO. 17, comprising or consisting of an amino acid sequence selected from SEQ ID NO: 2, 4, 6, 8, 10, 12, 14, or 16 or a substantially similar amino acid sequence wherein the protein has at least 95%, at least 96%, at least 97%, at least 98%, or at least 99% sequence identity thereto, and is photocleavable and dissociates into at least two fragments, or releases one end of a loop insertion.

2. A nucleic acid encoding the photocleavable protein of claim 1, or comprising the nucleotide sequence of SEQ ID NO: 1, 3, 5, 7, 9, 11, 13, or 15.

3. A recombinant expression vector comprising a nucleic acid of claim 2, operably linked with transcriptional and translational regulatory regions or sequences to provide for expression of the nucleic acid in a host cell.

4. A host cell comprising the vector of claim 3.

5. A method of localizing a protein within a cell comprising the step of providing a photocleavable genetically encoded protein of claim 1, wherein one or more fragments comprises a localization tag or an exclusion tag, and photocleaving the protein.

6. The method of claim 5 adapted to modulate gene expression, wherein a dissociated fragment comprises a nuclear localization tag and a transcription factor.

7. A method of enzyme activation comprising the step of providing a photocleavable genetically encoded protein construct comprising protein of claim 1 and the enzyme and an enzyme inhibitor, wherein said protein construct spontaneously dissociates into at least two fragments following photocleavage, wherein a first fragment comprises the enzyme, and a second fragment comprises the inhibitor.

8. A method of purifying a protein of interest using a purification substrate having an affinity tag, comprising the step of providing a genetically encoded photocleavable protein of claim 1 and a sequence break consisting of a C-terminus and a N-terminus, wherein the protein spontaneously dissociates into two fragments following photocleavage, wherein one fragment comprises an affinity tag which specifically binds to the substrate affinity tag, and the other fragment comprises the protein of interest.

* * * * *